United States Patent
Solbakken et al.

(10) Patent No.: US 7,919,071 B2
(45) Date of Patent: *Apr. 5, 2011

(54) CONTRAST AGENT

(75) Inventors: Magne Solbakken, Oslo (NO); Torgrim Engell, Oslo (NO); Harry John Wadsworth, Amersham (GB); Colin M. Archer, Amersham (GB)

(73) Assignee: GE Healthcare AS, Oslo (NO)

( * ) Notice: Subject to any disclaimer, the term of this patent is extended or adjusted under 35 U.S.C. 154(b) by 885 days.

This patent is subject to a terminal disclaimer.

(21) Appl. No.: 10/541,949

(22) PCT Filed: Jan. 9, 2004

(86) PCT No.: PCT/NO2004/000002
§ 371 (c)(1),
(2), (4) Date: Jun. 7, 2006

(87) PCT Pub. No.: WO2004/062568
PCT Pub. Date: Jul. 29, 2004

(65) Prior Publication Data
US 2007/0020176 A1  Jan. 25, 2007

(30) Foreign Application Priority Data
Jan. 9, 2003 (NO) .................................. 20030115

(51) Int. Cl.
*A61K 51/00* (2006.01)
*A61M 36/14* (2006.01)
*A61B 6/00* (2006.01)
*C07D 257/04* (2006.01)

(52) U.S. Cl. ....... 424/1.65; 424/1.11; 600/436; 548/250
(58) Field of Classification Search .................. 424/1.1, 424/1.65; 600/436; 548/250
See application file for complete search history.

(56) References Cited

U.S. PATENT DOCUMENTS

| 5,688,487 A | * 11/1997 | Linder et al. | 424/1.65 |
| 6,264,914 B1 | * 7/2001 | Klaveness et al. | 424/1.65 |
| 7,052,672 B2 | * 5/2006 | Forster et al. | 424/1.65 |

FOREIGN PATENT DOCUMENTS

| JP | 9165378 | 6/1997 |
| WO | 9818496 | 5/1998 |
| WO | 0177145 | 10/2001 |
| WO | 0192283 | 12/2001 |
| WO | 02070018 | 9/2002 |
| WO | 03006070 | 1/2003 |
| WO | 03006491 | 1/2003 |

OTHER PUBLICATIONS

International Search Report for PCT/NO2004/000002 dated Jul. 2004.
International Preliminary Examination Report dated Mar. 2005.

* cited by examiner

*Primary Examiner* — Michael G Hartley
*Assistant Examiner* — Leah Schlientz

(57) ABSTRACT

The present invention relates to a contrast agent of Formula I V-L-Z Formula I where V is a non-peptidic vector having affinity for the Angiotensin II receptor, L is a bond, a spacer or a linker moiety and Z represents a moiety detectable in an in vivo imaging procedure of a human or animal body.

6 Claims, 1 Drawing Sheet

Figure 1 - The RAAS system

CONTRAST AGENT

Figure 1:
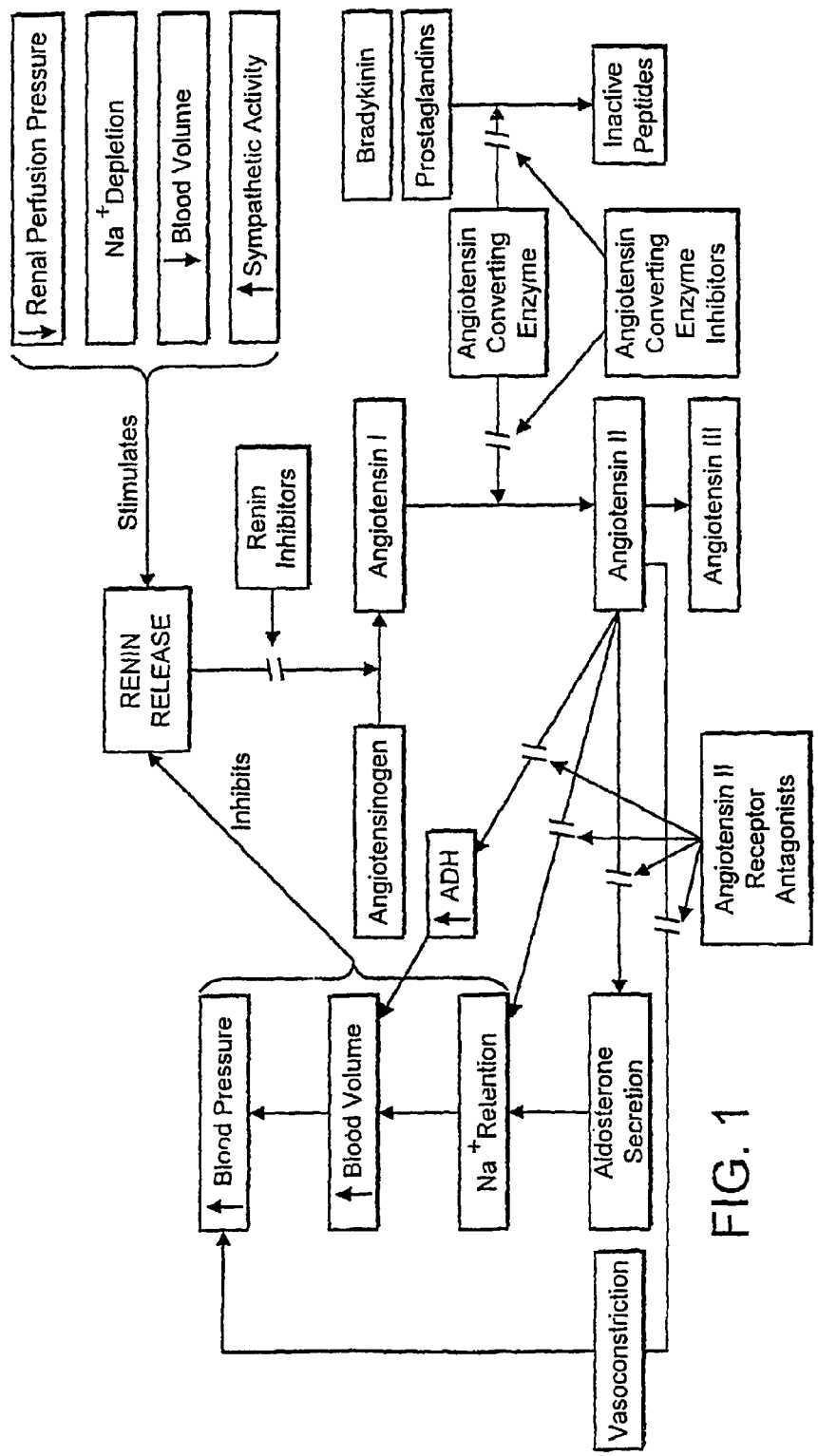

This application is a filing under 35 U.S.C. 371 of international application number PCT/NO2004/000002, filed Jan. 9, 2004, which claims priority to application number 20030115 filed Jan. 9, 2003, in Norway the entire disclosure of which is hereby incorporated by reference.

FIELD OF INVENTION

The present invention relates to diagnostic contrast agents suitable for use in diagnostic imaging techniques in which a disease state may be imaged using such contrast agents. More particularly the invention relates to contrast agents in which the targeting vector binds to angiotensin II receptors.

BACKGROUND OF INVENTION

Angiotensin II (Ang II)—the octapeptide (Asp-Arg-Val-Tyr-Ile-His-Pro-Phe)- is a pleiotropic vasoactive peptide that binds to two distinct receptors: the Ang II type 1 ($AT_1$) and type 2 ($AT_2$) receptors. Activation of the renin-angiotensin-aldostrone system (RAAS) results in vascular hypertrophy, vasoconstriction, salt and water retention, and hypertension. These effects are mediated predominantly by $AT_1$ receptors. Paradoxically, other Ang II-mediated effects, including cell death, vasodilation, and natriuresis, are mediated by $AT_2$ receptor activation. The understanding of Ang II signalling mechanisms remains incomplete. $AT_1$ receptor activation triggers a variety of intracellular systems, including tyrosine kinase-induced protein phosphorylation, production of arachidonic acid metabolites, alteration of reactive oxidant species activities, and fluxes in intracellular $Ca^{2+}$ concentrations. $AT_2$ receptor activation leads to stimulation of bradykinin, nitric oxide production, and prostaglandin metabolism, which are, in large part, opposite to the effects of the $AT_1$ receptor. (See: Berry C, Touyz R, Dominiczak A F, Webb R C, Johns D G.: Am J Physiol Heart Circ Physiol. 2001 December; 281(6):H2337-65. Angiotensin receptors: signalling, vascular pathophysiology, and interactions with ceramide).

Ang II is the active component of the renin-angiotensin-aldosterone system (RAAS). It plays an important physiological role in the regulation of blood pressure, plasma volume, sympathetic nervous activity, and thirst responses. Ang II also has a pathophysiological role in cardiac hypertrophy, myocardial infarction, hypertension, chronic obstructive pulmonary disease, liver fibrosis and atherosclerosis. It is produced systemically via the classical RAAS and locally via tissue RAAS. In the classical RAAS, circulating renal-derived renin cleaves hepatic-derived angiotensinogen to form the decapeptide angiotensin I (Ang I), which is converted by angiotensin-converting enzyme (ACE) in the lungs to the active Ang II. Ang I can also be processed into the heptapeptide Ang-(1-7) by tissue endopeptidases.

The RAAS system is illustrated schematically in FIG. 1 hereto which is based on FIG. 1 in the article by Foote et al. in Ann. Pharmacother. 27: 1495-1503 (1993).

In addition to the RAAS playing an important role in the normal cardiovascular homeostasis, over activity of the RAAS has been implicated in the development of various cardiovascular diseases, such as hypertension, congestive heart failure, coronary ischemia and renal insufficiency. After myocardial infarction (MI), RAAS becomes activated. Specifically the $AT_1$ receptor seems to play a prominent role in post-MI remodelling, since $AT_1$ receptor expression is increased after MI and in left ventricular dysfunction. Therefore drugs that interfere with RAAS, such as ACE inhibitors and $AT_1$ receptor antagonists, have been shown to be of great therapeutic benefit in the treatment of such cardiovascular disorders.

For heart, kidneys, lungs and liver alike, fibrosis represents a common pathway to their failure. Understanding pathophysiologic mechanisms involved in organ fibrosis is therefore of considerable interest, particularly given the potential for protective pharmacological strategies. Tissue repair involves inflammatory cells, including members of the monocyte/macrophage lineage, integral to initiating the repair process; and myofibroblasts, phenotypically transformed interstitial fibroblasts, responsible for collagen turnover and fibrous tissue formation. Each of these cellular events in the microenvironment of repair are associated with molecular events that lead to the de novo generation of angiotensin II (Ang II). In an autocrine/paracrine manner, this peptide regulates expression of TGF-beta 1 via angiotensin ($AT_1$) receptor-ligand binding. It is this cytokine that contributes to phenotypic conversion of fibroblasts to myofibroblasts (myoFb) and regulates myofibroblast turnover of collagen. Angiotensin-converting enzyme (ACE) inhibition or $AT_1$ receptor antagonism each prevent many of these molecular and cellular responses that eventuate in fibrosis and therefore have been found to be protective interventions.

(See: Weber K T. Fibrosis, a common pathway to organ failure: angiotensin II and tissue repair. Semin Nephrol. 1997 September; 17(5):467-91 and references therein).

Ang II may regulate tissue fibrosis via the activation of mesenchymal cells. For example, Ang II stimulates the proliferation of cardiac fibroblasts in vitro via activation of $AT_1$. The presence of $AT_1$ receptors has also been demonstrated on cardiac fibroblasts in vitro. Most of the profibrotic effects of Ang II appear to be mediated via this receptor; however, increased $AT_2$ expression on cardiac fibroblasts has been detected in hypertrophied human heart, and the balance between the expressions of these two subtypes may be critical in determining the response to Ang II.

(See: Am. J. Respir. Crit. Care Med., Volume 161, Number 6, June 2000, 1999-2004 Angiotensin II Is Mitogenic for Human Lung Fibroblasts via Activation of the Type 1 Receptor Richard P. Marshall, Robin J. McAnulty, and Geoffrey J. Laurent and references therein).

The Ang II receptors can be distinguished according to inhibition by specific antagonists. $AT_1$ receptors are selectively antagonized by biphenylimidazoles, such as Losartan, whereas tetrahydroimidazopyridines specifically inhibit $AT_2$ receptors. The $AT_2$ receptor may also be selectively activated by CGP-42112A. This is a hexapeptide analog of Ang II, which may also inhibit the $AT_2$ receptor, depending on concentration). Two other angiotensin receptors have been described: $AT_3$ and $AT_4$ subtypes.

In rodents, the $AT_1$ receptor has two functionally distinct subtypes, $AT_{1A}$ and $AT_{1B}$, with >95% amino acid sequence homology.

The second major angiotensin receptor isoform is the $AT_2$ receptor. It has low amino acid sequence homology (~34%) with $AT_{1A}$ or $AT_{1B}$ receptors. Although the exact signalling pathways and the functional roles of $AT_2$ receptors are unclear, these receptors may antagonize, under physiological conditions, $AT_1$-mediated actions inhibiting cell growth and by inducing apoptosis and vasodilation. The exact role of $AT_2$ receptors in cardiovascular disease remains to be defined.

Other receptors for Ang II besides $AT_1$ and $AT_2$ are known and are generally referred to as $AT_{atypical}$ (see Kang et al., Am. Heart J. 127:1388-1401 (1994)).

DESCRIPTION OF RELATED ART

WO 98/18496 (Nycomed Imaging AS) discloses contrast agents comprising Ang Il-receptor antagonists labelled for in vivo imaging.

U.S. Pat. No. 5,138,069 discloses substituted imidazoles for use as Ang II receptor blockers. Further, U.S. Pat. No. 5,264,581 (Cariani) discloses radioiodinated imidazole Ang II antagonists.

THE PRESENT INVENTION

It has now been found that Ang Il-receptor antagonists such as e.g. Losartan, Valsartan, Candesartan and Eprosartan and derivatives thereof labelled with a moiety or moieties detectable in vivo are useful diagnostic imaging agents for in vivo imaging of a human or animal body.

The contrast agents of the present invention are useful in imaging of Ang II receptor sites in vivo i.e. using targeted contrast agents in which the targeting vector has affinity for Ang II-receptor sites. The Ang II receptors are generally located within the cardiovascular system and are accessible to such contrast agents when they are administered into the blood stream. Accordingly, using such targeted contrast agents it is possible to detect diseases and disorders such as heart failure, atherosclerosis and restricted blood flow, as well as other vascular diseases and disorders, and diseases where fibrosis is prominent, and also to monitor the progression of treatment for such diseases and disorders.

DETAILED DESCRIPTION OF THE INVENTION

In a first aspect, the present invention provides a contrast agent as defined by formula I, V-L-Z    (Formula I)

wherein V is a non-peptidic vector having affinity for the Angiotensin II-receptor, L represents a bond, a spacer or linker and Z represents a moiety detectable in an in vivo imaging procedure of a human or animal body.

The vector V is a non-peptidic targeting moiety having affinity for the Ang II receptor. V further represents an imidazole Ang II anatagonist such as e.g. Losartan, Valsartan, Caldesartan and Eprosartan and derivatives thereof.

The role of the linker L is to couple vector to the imaging moiety, and where L is a spacer moiety the role of L is to distance a relatively bulky imaging moiety, Z, from the active site of the vector, V.

A linker moiety may serve to link one vector to one imaging moiety; alternatively it may link together more than one vector and/or more than one imaging moiety. Likewise an imaging moiety or a vector may be linked to more than one linker. Use in this way of a plurality of imaging moieties (e.g. several linker-imaging moieties attached to one vector or several imaging moieties attached to one linker itself attached to one vector) may enable the detectability of the contrast agent to be increased (e.g. by increasing its radioopacity, echogenicity or relaxivity) or may enable it to be detected in more than one imaging modality. Use in this way of a plurality of vectors may e.g. increase the targeting efficiency of a contrast agent or may make the contrast agent/therapeutic agent able to target more than one site, e.g. different receptors for an agent which has receptor heterogeneity.

The linker moiety L may be a simple bond, glutaric acid, diglycolic acid, PEG units, PEG-like linkers or may be represented by other linkers well known in the art, e.g. as described in WO 01/77145 pages 2327, the content of which are incorporated herein by reference. L may also be represented by a combination of the linker units.

The imaging moieties (Z) in the compounds of the invention may be any moiety capable of detection either directly or indirectly in an in vivo diagnostic imaging procedure.

For pharmaceuticals useful in diagnosis and particularly in in vivo diagnosis the moiety Z must be able to carry the imageable moiety or moieties denoted M. By carrying is meant any form of association between the moiety Z and M such as a chemical bond, e.g. covalent bond or electrovalent or ionic bonds or by absorption or any other kind of association.

Chelating agent of formula (II) and (e) hereafter are particularly preferred.

M can be any imageable moiety. The nature of M will depend of the imaging modality utilised in the diagnosis. M must be capable of detection either directly or indirectly in an in vivo diagnostic imaging procedure. eg. moieties which emit or may be caused to emit detectable radiation (eg. by radioactive decay, fluorescence excitation, spin resonance excitation, etc.), moieties which affect local electromagnetic fields (eg. paramagnetic, superparamagnetic, ferrimagnetic or ferromagnetic species), moieties which absorb or scatter radiation energy (eg. chromophores, particles (including gas or liquid containing vesicles), heavy elements and compounds thereof, etc.), and moieties which generate a detectable substance (eg. gas microbubble generators).

A wide range of suitable imageable moieties are known from e.g. WO 98/18496, the content of which is incorporated by reference.

Imaging modalities and imageable moieties M are described in more detail hereinafter:

In a first embodiment, the compound of formula (I) comprises a moiety Z carrying one or more imageable moieties M useful in the Radio and SPECT imaging modality. Preferably M is a gamma emitter with low or no alpha- and beta-emission and with a half-life of more than one hour. Preferred groups M are the radionuclides $^{67}$Ga, $^{111}$In, $^{123}$I, $^{125}$I, $^{131}$I, $^{81m}$Kr, $^{99}$Mo, $^{99m}$T, $^{201}$Tl and $^{133}$Xe. Most preferred is $^{99m}$Tc.

When M denotes a metallic radionuclide then Z comprises a chelating agent suitable for forming a stable chelate with M. Such chelating agents are well known from the state of art and typical examples of such chelating agents are described in Table I of WO 01/77145.

Particularly preferred are chelating agents of Formula II

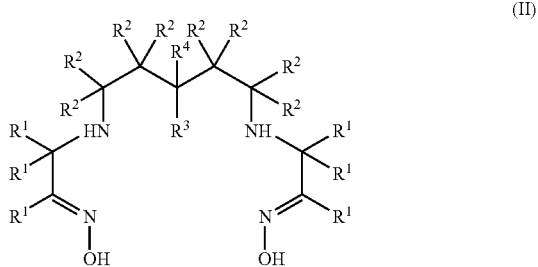

where:
each $R^1$, $R^2$, $R^3$ and $R^4$ is independently an R group;
each R group is independently H or $C_{1-10}$ alkyl, $C_{3-10}$ alkylaryl, $C_{2-10}$ alkoxyalkyl, $C_{1-10}$ hydroxyalkyl, $C_{1-10}$ alkylamine, $C_{1-10}$ fluoroalkyl, or 2 or more R groups, together with the atoms to which they are attached form a carbocyclic, heterocyclic, saturated or unsaturated ring.

More preferred are chelating agent represented by formulas a, b, c and d.

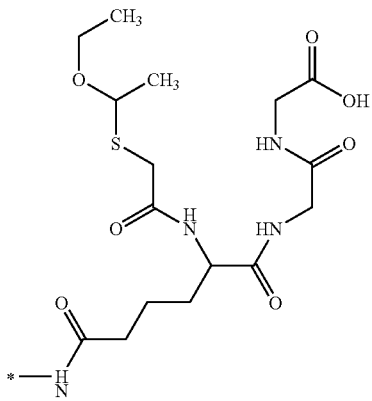

a

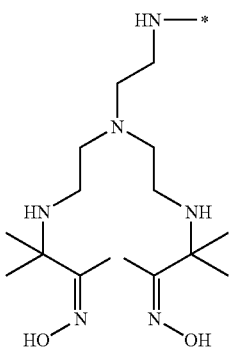

b

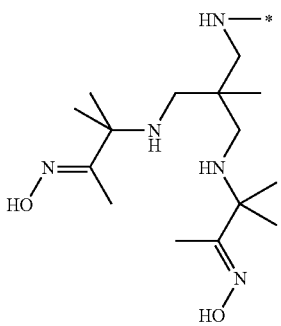

c

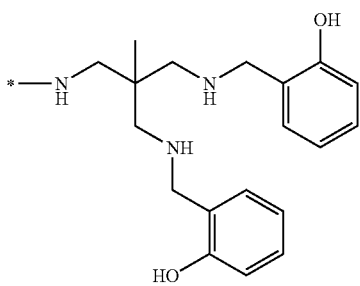

d

An even more preferred example a chelating agent is represented by formula e, herein denoted cPn216. Most preferred for Z is when the chelating agent is cPn216 and imaging moiety M is $^{99m}$Tc

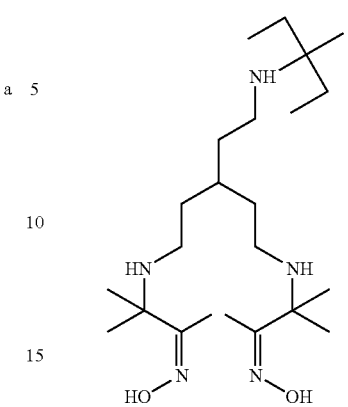

e

Conjugates comprising chelating agents of Formula II can be radiolabelled to give good radiochemical purity, RCP, at room temperature, under aqueous conditions at near neutral pH. An advantage of radiolabelling the conjugates at room temperature Is a simplified procedure in a hospital pharmacy. For the synthesis of chelating agent of formula II it is referred to WO 03/006070, the content of which are incorporated herein by reference.

Non-metal radionuclides such as $^{123}$I, $^{125}$I and $^{131}$I may be covalently linked to the moiety Z a substitution or addition reaction well known from the state of art.

In a second embodiment, the compound of formula (I) comprises a moiety Z carrying one more imageable moieties M useful in the PET imaging modality. M then denotes a radioemitter with positron-emitting properties. Preferred groups M are the radionuclides $^{11}$C, $^{18}$F, $^{68}$Ga, $^{13}$N, $^{15}$O and $^{82}$Rb. $^{18}$F is specifically preferred.

When M denotes a metallic radionuclide then Z comprises a chelating agent suitable for forming a stable chelate with M. Such chelating agents are well known from the state of art and typical examples of such chelating agents are described in Table I of WO 01/77145 and to the previous part on Radio and SPECT imaging.

In another preferred embodiment Z is the DOTA chelating agent and M is $^{68}$Ga which can readily introduced in to the chelate using microwave chemistry.

Non-metal radionuclides such as $^{18}$F may be covalently linked to the moiety Z by a substitution or addition reaction well known from the state of art and also described eg. in WO03/080544 which is hereby incorporated by reference.

In a third embodiment, the compound of formula (I) comprises a moiety Z carrying one or more imageable moieties M useful in the MR imaging modality. M here denotes a paramagnetic metal such those mentioned in U.S. Pat. No. 4,647,447, $Gd^{3+}$, $Dy^{3+}$, $Fe^{3+}$ and $Mn^{2+}$ are particularly preferred and Z comprises a chelating agent, in particular a chelating agent such as acyclic or cyclic polyaminocarboxylates (e.g. DTPA, DTPA-BMA, DOTA and DO3A as described e.g. in U.S. Pat. No. 4,647,447 and WO 86/02841. M may also denote metal oxide such as superparamagnetic, ferrimagnetic or ferromagnetic species which are absorbed by e.g. such that Z function as a coating to the metal oxide. Metal oxides for use as MR control agents are described e.g. in U.S. Pat. No. 6,230,777 which Is hereby incorporated by reference.

In a fourth embodiment the compound of formula (I) comprises a moiety Z carrying one or more imageable moieties M useful in the X-ray imaging modality. M here denotes a heavy metal such as W, Au and Bi preferably in the form of oxides which may be absorbed to Z. Iodinated aryl derivatives are particularly well known as X-ray contrast agents, e.g. Iopamiron™ and Omnipaque™.

Ultrasound imaging agents in the form of gas filled microvesicles can be utilised in the imaging of receptors e.g. when they are functionalised for binding to the vector V as described in the state of art e.g. in WO98/18500.

The imaging moiety Z may also represent a chromophore to be used in light imaging procedure. By chromophore is meant a group in a composition of matter, e.g. an organic or inorganic group which absorbs and/or emits light.

By light is meant electromagnetic radiation having wavelengths from 300-1300 nm.

Chromophores having absorption and/or emission maxima in the visible to far infrared range are particularly relevant.

Use of contrast agents for optical imaging with affinity for biological targets can further be provided following the procedures in the state of art e.g. as described in WO 96/17628 which is herewith incorporated by reference.

The invention may be exemplified by Losartan derivatives and is based on attachment of linker (L) and imaging moieties (Z) to the imidazol 5-position. The principle also applies to other compounds having structural similarities, e.g. Valsartan, Candesartan and Eprosartan, possessing suitable anchoring sites in the part of the molecule corresponding to the Losartan imidazole ring.

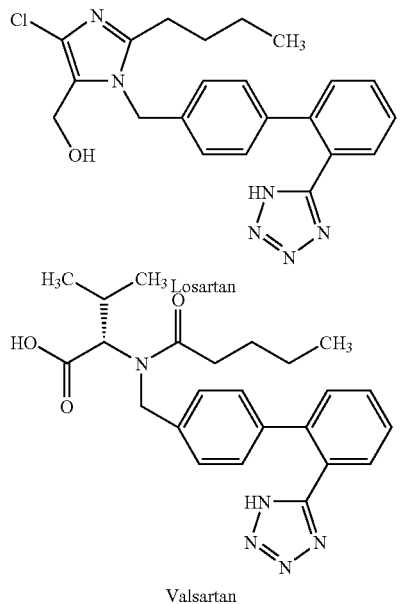

Losarta

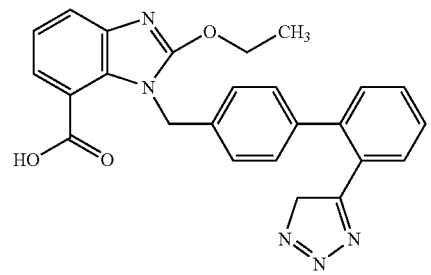

Candesartan

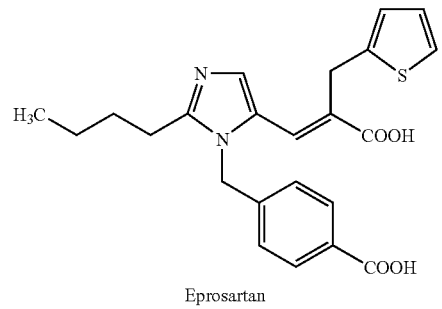

Eprosartan

Scheme 1 shows an example of how the imidazole 5-position can be used to anchor a chelating agent of formula e to give a derivatised Losartan molecule for Tc-chelation. Parent Losartan molecule is transformed to the azide-derivative followed by reduction to the corresponding amine. The amine is reacted with diglycolic anhydride, followed by activation and reaction with a suitable derivative of the chelating agent of formula e.

Scheme 1

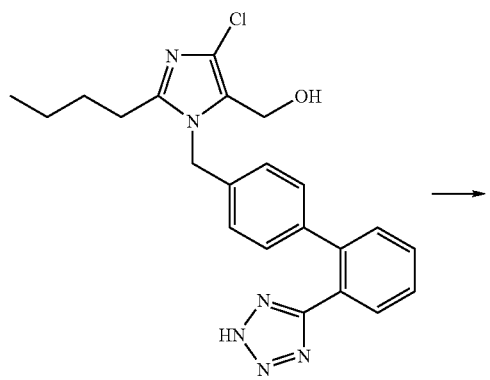

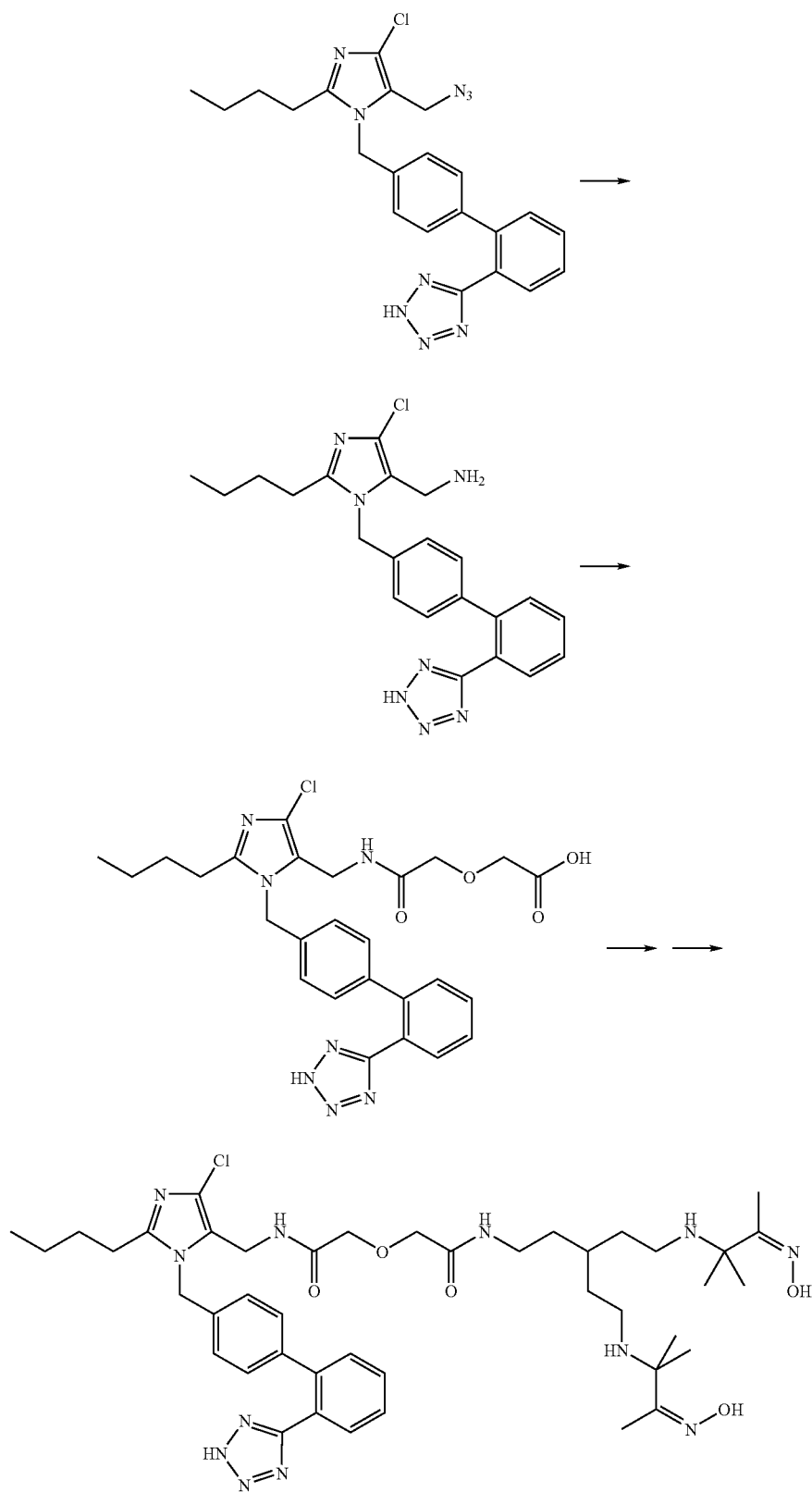
Scheme 2 shows an example of the solid phase synthesis of Losartan linker chelating agent conjugate.

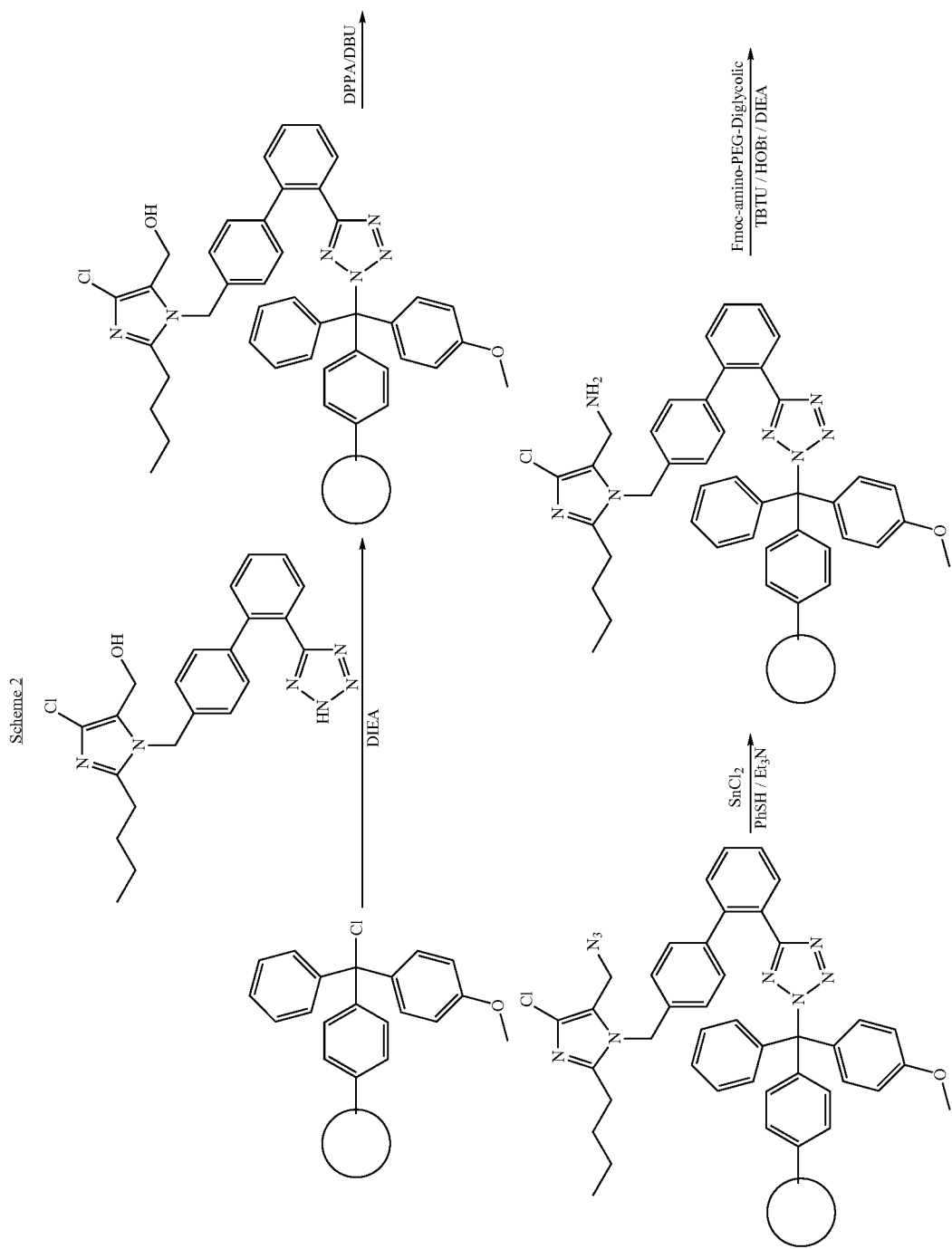

-continued
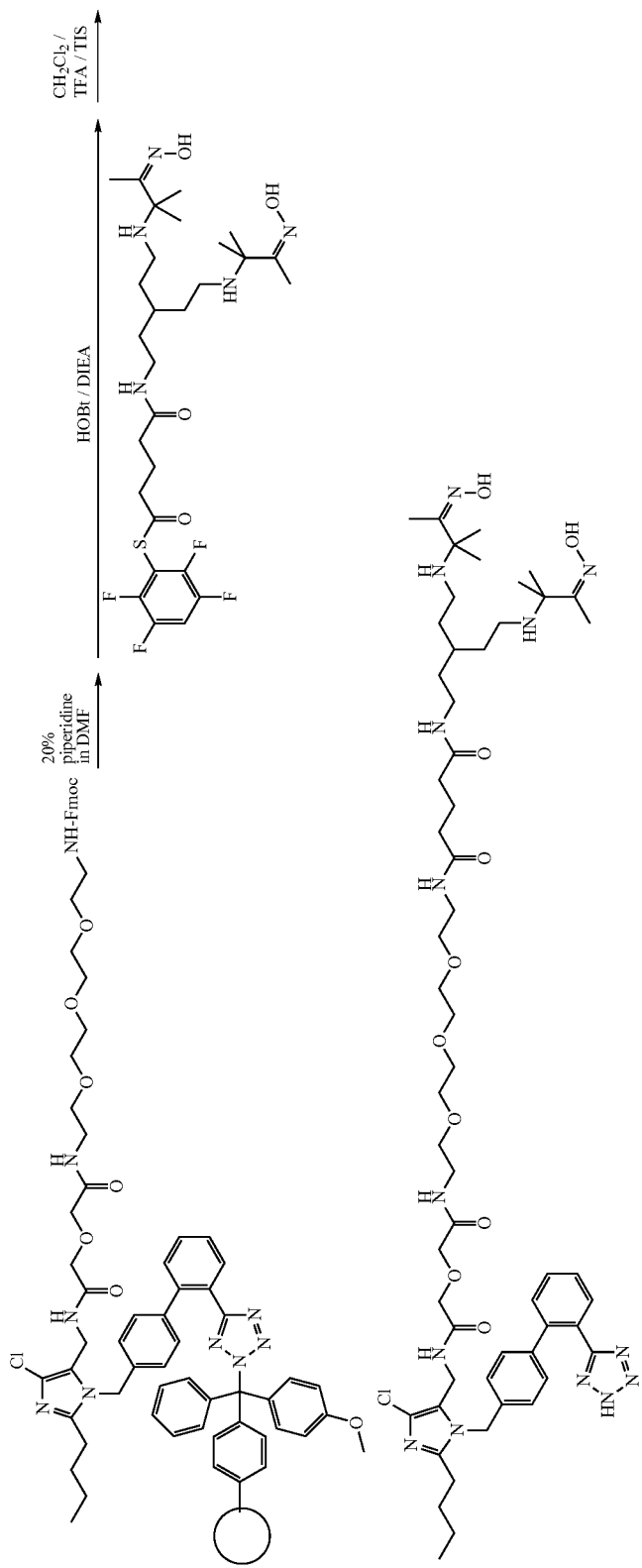

Other examples of related structures are shown below;

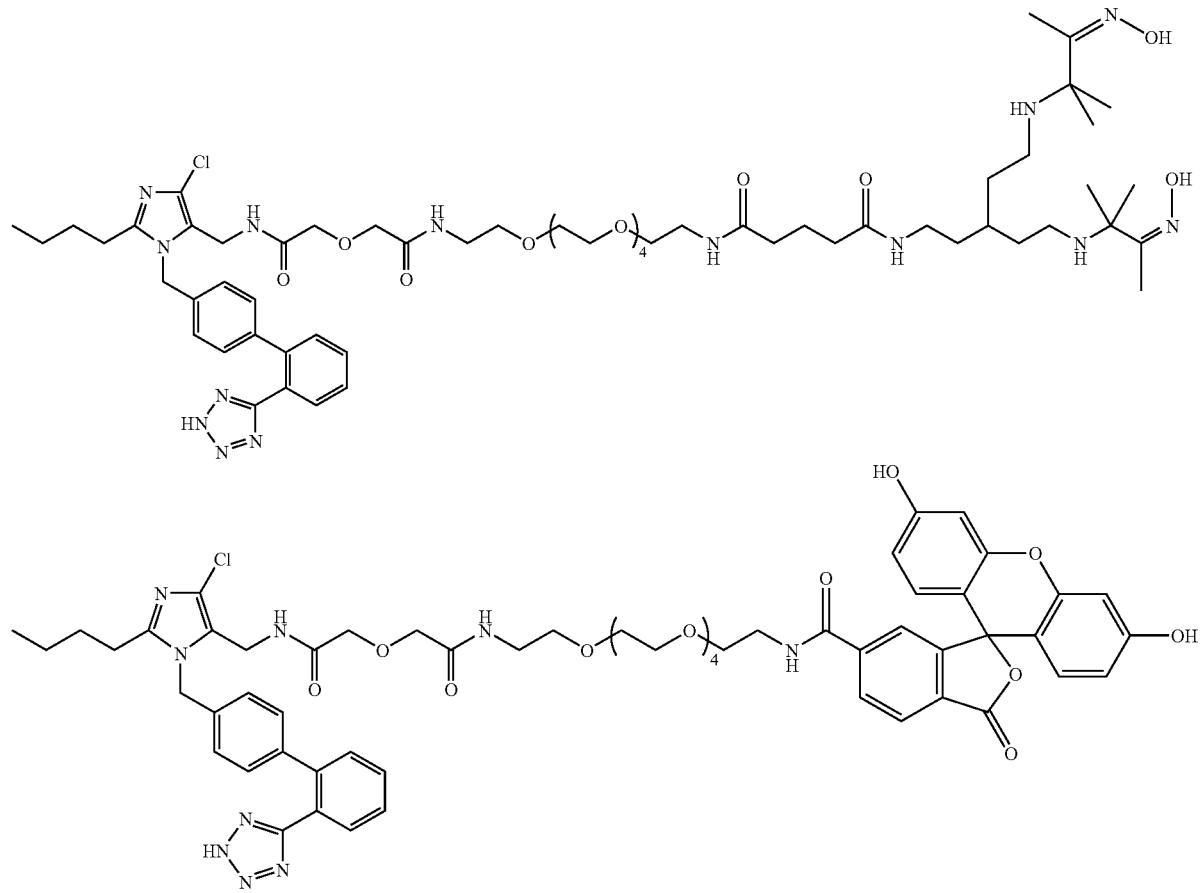

The contrast agent of formula (I) are preferably administered as a pharmaceutical formulation comprising the compound of formula (I) in a form suitable for administration to a mammal, such as a human. The administration is suitable carried out by injection or infusion of the formulation such as an aqueous solution. The formulation may contain one or more pharmaceutical acceptable additives and/or excipients e.g. buffers; solubilisers such as cyclodextrins; or surfactants such as Pluronic, Tween or phospholipids. Further; stabilisers or antioxidants such as ascorbic acid, gentisic acid or para-aminobenzoic acid and also bulking agents for lyophilisation such as sodium chloride or mannitol may be added.

The present invention also provides a pharmaceutical composition comprising an effective amount (e.g. an amount effective for enhancing Image contrast in an in vivo imaging procedure) of a composition of general formula I or a salt thereof, together with one or more pharmaceutically acceptable adjuvants, excipients or diluents.

Viewed from a further aspect the invention provides the use of a composition of formula I for the manufacture of a contrast medium for use in a method of diagnosis involving administration of said contrast medium to a human or animal body and generation of an image of at least part of said body.

Viewed from a still further aspect the invention provides a method of generating enhanced images of a human or animal body previously administered with a contrast agent composition comprising a composition of matter as defined by formula I, which method comprises generating an image of at least part of said body.

The invention further provides a method for the monitoring of the effect of treatment of heart failure and other diseases associated with up-regulation of the $AT_1$ receptor.

In still another aspect the invention provides a kit for the preparation of a radiopharmaceutical composition of formula (I) comprising a ligand-chelate conjugate and a reducing agent. Preferably the reducing agent is a stannous salt. The kit may further comprise one or more stabilisers, antioxidants, bulking agents for lyophilisation and solubilisers.

The meaning of abbreviations used herein is as follow:
DOTA—1,4,7,10-tetraazacyclododecan-1,4,7,10-tetraacetic acid
PEG—polyethyleneglycol
DIEA—N,N-diisopropylethylamine
DPPA—diphenylphosphoryl azide
DBU—1,8-diaza-bicyclo(5,4,0)undec-7-ene
DMF—dimethyl formamide
MDP—methylene diphosphonate
TFA—trifluoroacetic acid
THF—tetrahydro furan
HATU—N-[(dimethylamino)-1H-1,2,3-triazolo[4,5-b]pyridino-1-ylmethylene]-N-methylmethanaminium hexafluorophosphonate N-oxide
Fmoc—9-fluorenylmethoxycarbonyl
Boc—t-butoxycarbonyl
TBTU—2-(1H-Benzotriazole-1-yl)-1,1,3,3-tetramethyluronium tetrafluoroborate
HOBt—N-hydroxybenzotriazole TIS—Triisopropylsilan
NMP—N-Methylpyrrolidone
MDP—methylene diphosphonate The invention is further illustrated by the following non-limiting examples:

EXAMPLES

Example 1

Losartan Derivatised with Biotin

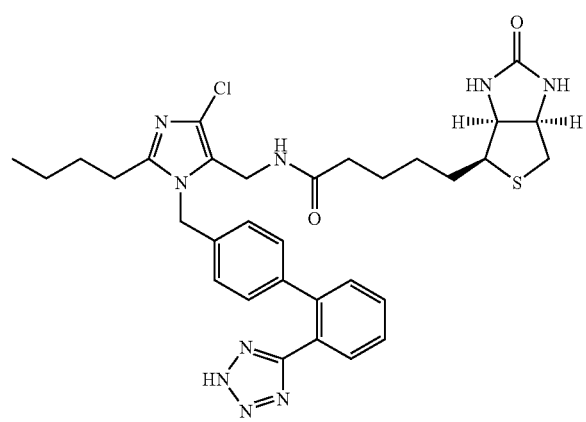

a) Replacement of Losartan Hydroxyl Group by Azide

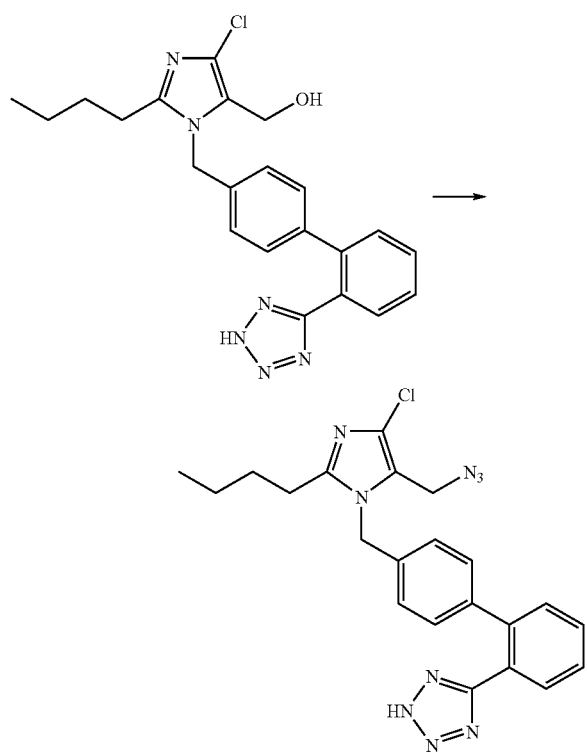

To a stirred suspension of Losartan (MSD, 0.423 g, 1.00 mmol) and diphenylphosphoryl azide (Aldrich, 0.259 ml, 1.20 mmol) in tetrahydrofuran (8 ml) was added DBU (0.329 ml, 2.20 mmol). After stirring overnight water/acetonitrile (1:1, 4.8 ml) was added and the mixture was filtered. After addition of neat TFA (to pH 2) the mixture was purified by preparative HPLC (column Phenomenex Luna C18(2) 5 µm 21.2×250 mm, solvents: A=water/0.1% TFA and B=acetonitrile/0.1% TFA; gradient 35-45% B over 60 min; flow 10.0 ml/min, UV detection at 214 nm) in several runs to give 99 mg (22%) of the product as white crystals after lyophilisation. Analysis by LC-MS (column Phenomenex Luna C18(2) 3 µm 50×4.60 mm, solvents: A=water/0.1% TFA and B=acetonitrile/0.1% TFA; gradient 20-80% B over 10 min; flow 1 ml/min, UV detection at 214 nm, ESI-MS) gave a peak at 7.3 minutes with m/z 448.1 (MH$^+$) corresponding to the structure.

b) Reduction of the Azide Group to Amino Function

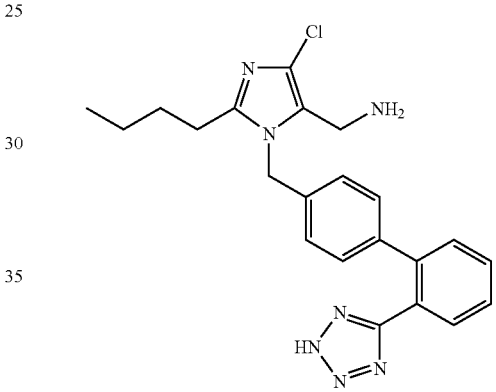

To a solution of compound from a) (5.0 mg, 0.011 mmol) in methanol (3 ml) was added Pd/C (Koch-Light, ca 10 mg). The mixture was stirred under hydrogen (1 atm) for 10 min, filtered and concentrated. The residue was used in the next step without further work up. LC-MS analysis (column Phenomenex Luna C18(2) 3 µm 50×4.60 mm, solvents: A=water/0.1% TFA and B=acetonitrile/0.1% TFA; gradient 20-80% B over 10 min; flow 1 ml/min, UV detection at 214 nm, ESI-MS) gave a peak at 1.9 minutes with m/z 422.2 (MH$^+$) corresponding to the amine.

c) Conjugation of Biotin

Biotin (Fluka, 3.0 mg, 0.011 mmol) was activated with HATU (Applied Biosystems, 4.0 mg, 0.011 mmol) and DIEA (2M in NMP, 11 µl, 0.022 mmol) in DMF (1 ml) for 10 min. The mixture was added to a solution of compound b) (0.011 mmol) in DMF (0.5 ml). After 45 minutes reaction time the product was purified by preparative HPLC (column Phenomenex Luna C18(2) 5 µm 21.2×250 mm, solvents: A=water/0.1% TFA and B=acetonitrile/0.1% TFA; gradient 20-60% B over 60 min; flow 10.0 ml/min, UV detection at 214 nm), giving 2.0 mg (28%) of product after lyophilisation. LC-MS analysis (column Phenomenex Luna C18(2) 3 µm 50×4.60 mm, solvents: A=water/0.1% TFA and B=acetonitrile/0.1% TFA; gradient 10-80% B over 10 min; flow 1 ml/min, UV detection at 214 nm, ESI-MS) gave a peak at 10.6 minutes with m/z 648.6 (MH$^+$) corresponding to the structure.

Example 2

Losartan Derivatised with Fluorescein

NHS-Fluorescein (Pierce, 6.0 mg, 0.014 mmol) and DIEA (2M in NMP, 14 μl, 0.028 mmol) were added to a solution of amino functionalized losartan from Example 1 b) (0.014 mmol) in DMF (1.5 ml). The reaction mixture was left over night. The product was purified by preparative HPLC (column Phenomenex Luna C18(2) 5 μm 21.2×250 mm, solvents: A=water/0.1% TFA and B=acetonitrile/0.1% TFA; gradient 20-80% B over 60 min; flow 10.0 ml/min, UV detection at 214 nm) giving 4.0 mg (37%) after lyophilisation. LC-MS analysis (column Phenomenex Luna C18(2) 3 μm 50×4.60 mm, solvents: A=water/0.1% TFA and B=acetonitrile/0.1% TFA; gradient 20-80% B over 10 min; flow 1 m/min, UV detection at 214 nm, ESI-MS) gave a peak at 10.4 minutes with m/z 780.8 (MH$^+$) corresponding to the structure.

Example 3

Losartan derivatised with Glutaric Acid Modified cPn216 for Tc-Labelling a) Synthesis of cPn216-Glutaric Acid Intermediate

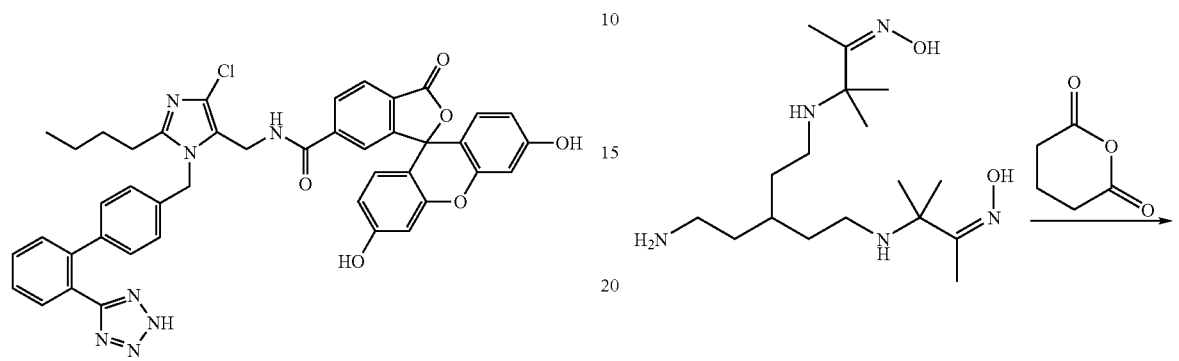

cPn216 (100 mg, 0.29 mmol) was dissolved in DMF (10 mL) and glutaric anhydride (33 mg, 0.29 mmol) added by portions with stirring. The reaction was stirred for 23 hours to afford complete conversion to the desired product. The pure acid was obtained following RP-HPLC in good yield.

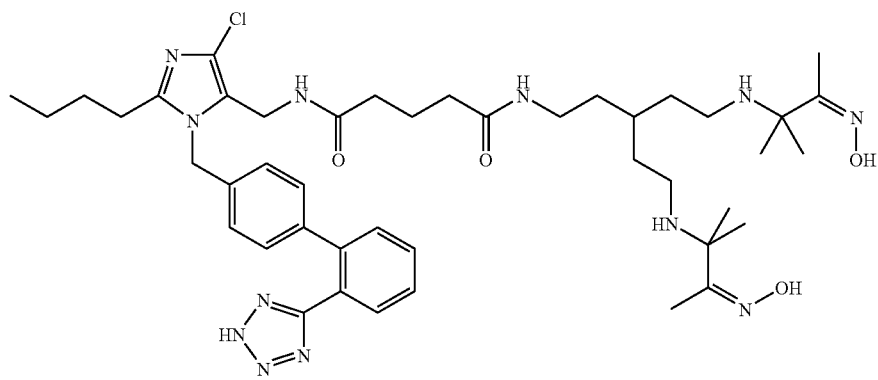

b) Synthesis of Tetrafluorothiophenyl Ester of cPn216-Glutaric Acid

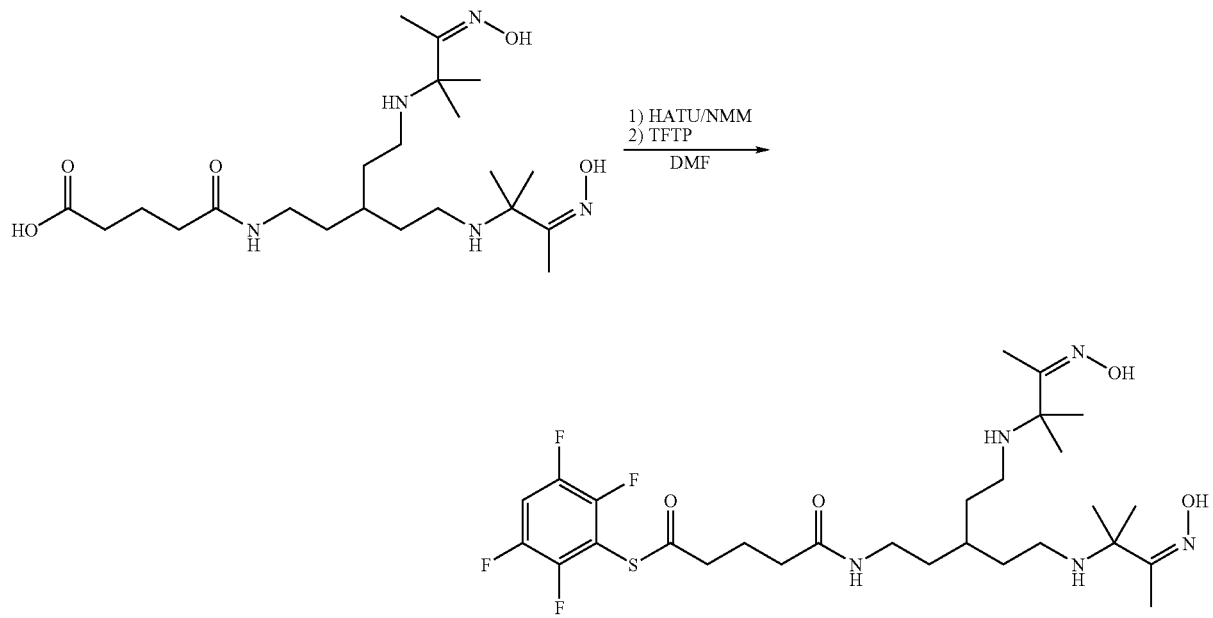

To cPn216-glutaric acid (300 mg, 0.66 mmol) in DMF (2 mL) was added HATU (249 mg, 0.66 mmol) and NMM (132 µL, 1.32 mmol). The mixture was stirred for 5 minutes then tetrafluorothiophenol (0.66 mmol, 119 mg) was added. The solution was stirred for 10 minutes then the reaction mixture was diluted with 20% acetonitrile/water (8 mL) and the product purified by RP-HPLC yielding 110 mg of the desired product following freeze-drying.

c) Coupling of cPn216-Glutaric Acid Active Ester to Amino Derivatised Losartan

To a solution of amino derivatised Losartan from Example 1b) (10 µmol) in DMF (1 ml) was added N-methylmorpholine (3.3 µl, 30 µmol), cPn216-glutaric acid tetrafluorothiophenyl ester from b) (6.8 mg, 11 µmol, prepared from cPn216 and glutaric acid anhydride by standard methods. After 45 min the reaction mixture was concentrated. The residue was taken up in acetonitrile/water and purified by preparative HPLC (column Vydac 218TP1022 C18 10 µm, 22×250 mm, solvents: A=water/0.1% TFA and B=acetonitrile/0.1% TFA; gradient 10-40% B over 60 min; flow 10.0 ml/min, UV detection at 214 nm) giving 4.2 mg (49%) of product after lyophilisation. LC-MS analysis (column Phenomenex Luna C18(2) 3 □m 2.0×50 mm, solvents: A=water/0.1% HCOOH and B=acetonitrile/0.1% HCOOH; gradient 10-40% B over 10 min; flow 0.3 ml/min, UV detection at 214 and 254 nm, ESI-MS) gave a peak at 6.2 min with m/z at 861.6 (MH$^+$) as expected. Further characterisation was carried out by NMR spectroscopy confirming the structure.

Example 4

Losartan Derivatised with Diglycolic Acid Modified Pn216 for Tc-Labelling

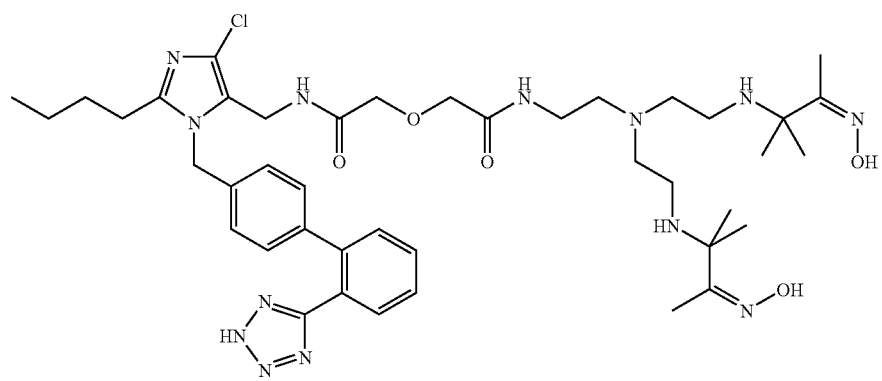

a) Acylation with Diglycolic Anhydride

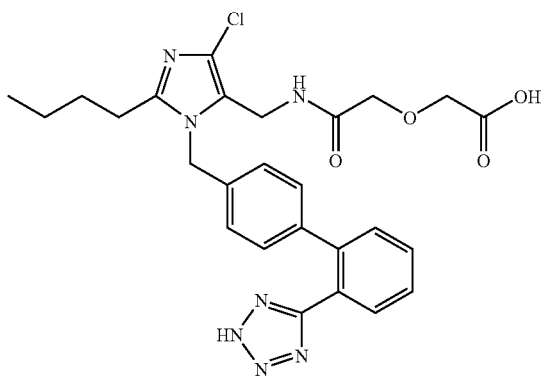

Azide derivatised Losartan from Example 1a) (0.12 mmol) was reduced to the corresponding amine as described under Example 1b). The catalyst was filtered off and diglycolic anhydride (Acros, 70 mg, 0.60 mmol) was added directly to the methanolic solution. After stirring overnight the mixture was concentrated and the residue was purified by preparative HPLC (column Vydac 218TP1022 C18 10 μm 22×250 mm, solvents: A=water/0.1% TFA and B=acetonitrile/0.1% TFA; gradient 10-40% B over 60 min; flow 10.0 ml/min, UV detection at 254 nm) giving 30 mg (46% over two steps) of white, fluffy material after lyophilisation. Analysis by LC-MS (column Phenomenex Luna C18(2) 3 μm 2.0×50 mm, solvents: A=water/0.1% HCOOH and B=acetonitrile/0.1% HCOOH; gradient 10-80% B over 10 min; flow 0.3 ml/min, UV detection at 214 and 254 nm, ESI-MS) gave a peak at 6.7 min with m/z at 538.0 (MH$^+$) in accordance with the structure. Further characterisation was carried out by NMR spectroscopy.

b) Conjugation with Pn216

To a solution of Losartan derivative a) (5.4 mg, 0.010 mmol) and HATU (3.8 mg, 0.010 mmol) in DMF (1 ml) was added 2 M DIEA in NMP (15 μl, 0.030 mmol). The reaction mixture turned yellow and was stirred for 15 min. To the activated carboxylic acid was added a solution of Pn216 (3.4 mg, 0.010 mmol) in DMF (0.25 ml). Progress of the reaction was monitored by analytical HPLC (column Phenomenex Luna C18(2) 3 μm 4.6×50 mm, solvents: A=water/0.1% TFA and B=acetonitrile/0.1% TFA; gradient 10-40% B over 10 min; flow 2.0 ml/min, UV detection at 214 and 254 nm). After 1 hr reaction time a fresh aliquot of HATU (3 mg) was added. After 20 min the reaction had run to completion. The mixture was purified by preparative HPLC (column Vydac 218TP1022 C18 10 μm 22×250 mm, solvents: A=water/ 0.1% TFA and B=acetonitrile/0.1% TFA; gradient 10-40% B over 60 min; flow 10.0 ml/m in, UV detection at 254 nm) giving 4.3 mg (50%) of product after lyophilisation. LC-MS analysis (column Phenomenex Luna C18(2) 30m 2.0×50 mm, solvents: A=water/0.1% HCOOH and B=acetonitrile/ 0.1% HCOOH; gradient 10-40% B over 10 min; flow 0.3 ml/min, UV detection at 214 and 254 nm, ESI-MS) gave a peak at 6.0 min with m/z at 864.3 (MH$^+$) corresponding to the structure.

Example 5

Losartan Derivatised with Diglycolic Acid Modified cPn216 for Tc-Labelling

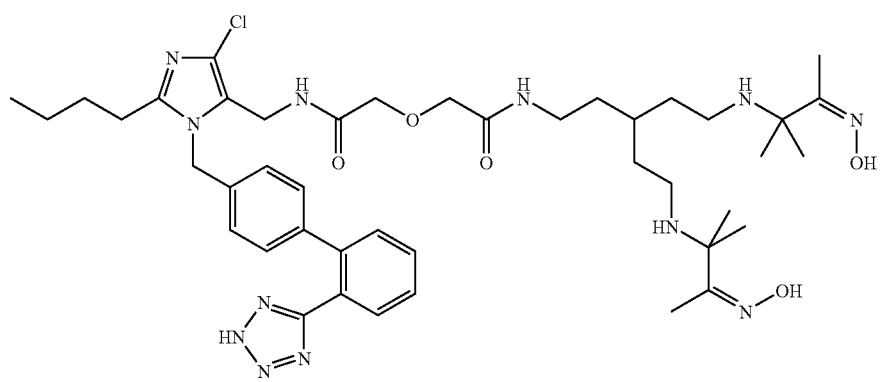

To a solution of Losartan derivative from Example 4a) (5.4 mg, 0.010 mmol) and HATU (3.8 mg, 0.010 mmol) in DMF (1 ml) was added 2 M DIEA in NMP (15 μl, 0.030 mmol). The reaction mixture turned yellow and was stirred for 15 min. To the activated carboxylic acid was added a solution of cPn216 (3.4 mg, 0.010 mmol) in DMF (0.25 ml). Progress of the reaction was monitored by analytical HPLC (column Phenomenex Luna C18(2) 3 μm 4.6×50 mm, solvents: A=water/0.1% TFA and B=acetonitrile/0.1% TFA; gradient 10-40% B over 10 min; flow 2.0 ml/min, UV detection at 214 and 254 nm). After addition of two more aliquots of HATU complete conversion of starting materiel was achieved. The mixture was purified by preparative HPLC (column Phenomenex Luna C18(2) 5 μm 21.2×250 mm, solvents: A=water/ 0.1% TFA and B=acetonitrile/0.1% TFA; gradient 10-40% B over 60 min; flow 10.0 ml/min, UV detection at 214 nm) to give 3.7 mg (43%) of product after lyophilisation. Analysis by LC-MS (column Phenomenex Luna C18(2) 3 μm 2.0×50 mm, solvents: A=water/0.1% HCOOH and B=acetonitrile/ 0.1% HCOOH; gradient 10-40% B over 10 min; flow 0.3 ml/min, UV detection at 214 and 254 nm, ESI-MS) gave a peak at 6.1 min with m/z at 863.2 (MH$^+$) in accordance with the structure. Further characterisation was carried out by NMR spectroscopy.

Example 6

Losartan Derivatised with Biotin Via a Peg Linker

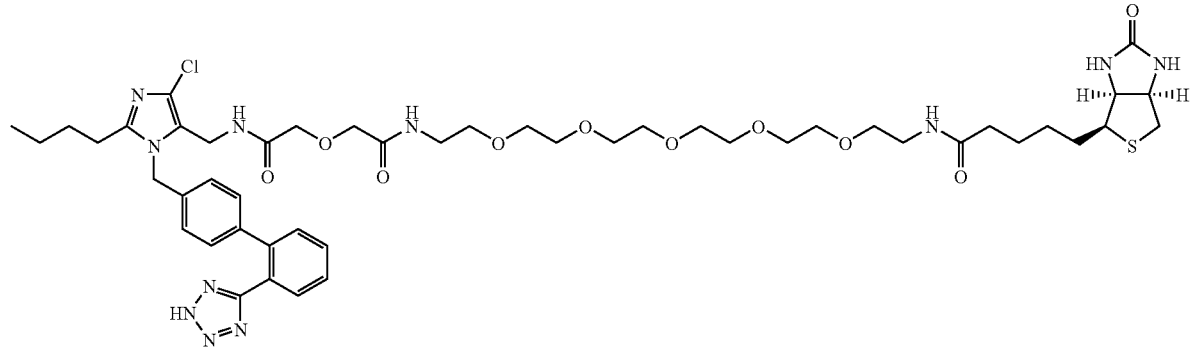

a) Conjugation of PEG

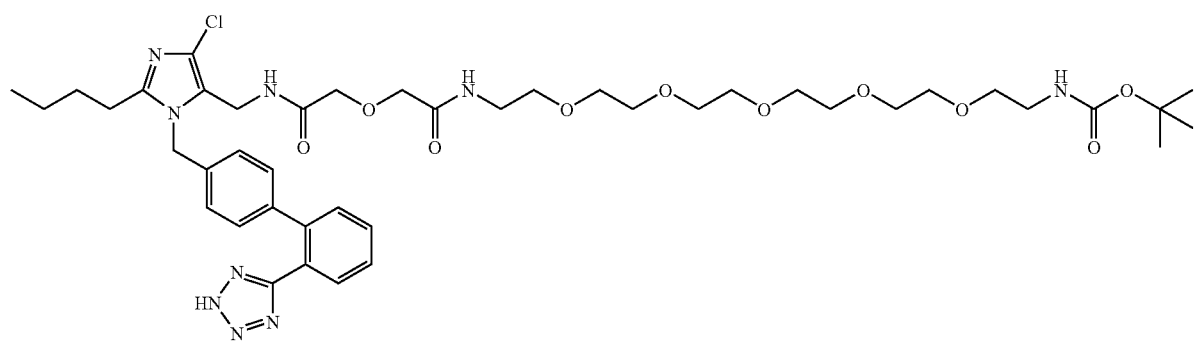

Boc-amino PEG acid (Polypure, 6.0 mg, 0.013 mmol) was activated with HATU (5.0 mg, 0.013 mmol) and DIEA (2M in NMP, 13 μl, 0.026 mmol) in DMF (1 ml) for 5 minutes. The mixture was added to a solution of compound from Example 1b) (0.013 mmol) in DMF (0.5 ml). After 1.5 hrs reaction time the solution was diluted with 30% acetonitrile in water (4 ml) and the product was purified by preparative HPLC (column Phenomenex Luna C18(2) 5 μm 21.2×250 mm, solvents: A=water/0.1% TFA and B=acetonitrile/0.1% TFA; gradient 30-60% B over 60 min; flow 10.0 m/min, UV detection at 214 nm) giving 5.5 mg (47%) of the product after lyophilisation. LC-MS analysis (column Phenomenex Luna C18(2) 3 μm 2.0×50 mm, solvents: A=water/0.1% TFA and B=acetonitrile/0.1% TFA; gradient 30-100% B over 10 min; flow 1 m/min, UV detection at 214 nm, ESI-MS) gave a peak at 7.0 minutes with m/z 900.9 (MH$^+$) corresponding to the structure.

b) Removal of Boc Protection Group

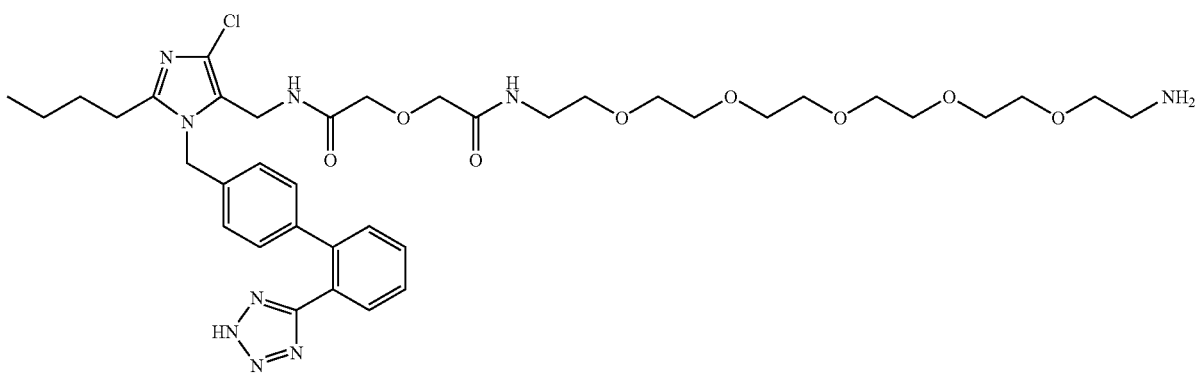

Compound a) (5.5 mg, 6.1 μmol) was dissolved in a 50% solution of TFA in dichloromethane (4 ml). Progress of the reaction was monitored by analytical HPLC (column Phenomenex Luna C18(2) 3 μm 4.6×50 mm, solvents: A=water/

0.1% TFA and B=acetonitrile/0.1% TFA; gradient 10-40% B over 10 min; flow 2.0 ml/min, UV detection at 214 and 254 nm) which proved that the cleavage was completed after 20 min, $t_R$=6.1 min. Analysis by MS (direct injection (solvents: A=water/0.1% TFA and B=acetonitrile/0.1% TFA; 50% B over 2 min; flow 0.3 ml/min, ESI-MS) gave m/z at 800.7 (MH$^+$) corresponding to the amine. The solution was concentrated and the product was used in the next step without further purification.

c) Conjugation of Biotin

Biotin (Fluka, 1.0 mg, 4.0 µmol) was activated with HATU (1.5 mg, 4.0 µmol) and DIEA (2M in NMP, 4.5 µl, 9.0 µmol) in DMF (1 ml) for 10 min and then added to a solution of compound b) (3.0 µmol) in DMF (1.5 ml). The reaction mixture was stirred for 15 min, diluted with 20% acetonitrile in water and purified by preparative HPLC (column Phenomenex Luna C18(2) 5 µm 21.2×250 mm, solvents: A=water/0.1% TFA and B=acetonitrile/0.1% TFA; gradient 20-60% B over 60 min; flow 10.0 ml/min, UV detection at 214 nm) giving 2.4 mg (81%) of product. Analysis by MS direct injection (solvents: A=water/0.1% TFA and B=acetonitrile/0.1% TFA; 50% B over 2 min; flow 0.3 ml/min, ESI-MS) gave m/z at 1026.8 (MH$^+$) corresponding to the structure.

Example 7

Losartan Derivatised with Fluorescein Via a PEG Linker

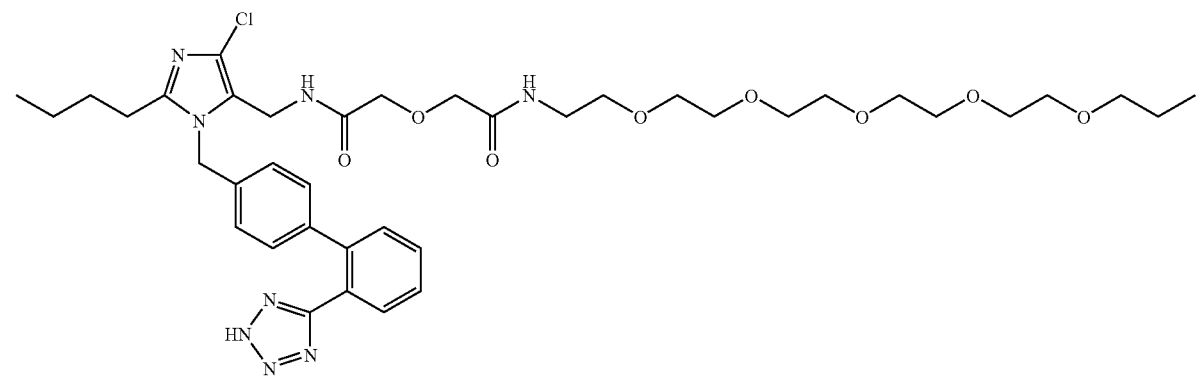

NHS-Fluorescein (Pierce, 2 mg, 4 µmol) and DIEA (2M in NMP, 4.5 µl, 9.0 µmol) were added to a solution of compound from Example 6 b) (3 µmol) in DMF (1.5 ml). The reaction was left over night. After dilution with 30% acetonitrile and adjustment of pH to 2 (TFA) the product was purified by preparative HPLC (column Phenomenex Luna C18(2) 5 µm 21.2×250 mm, solvents: A=water/0.1% TFA and B=acetonitrile/0.1% TFA; gradient 30-60% B over 60 min; flow 10.0 ml/min, UV detection at 214 nm) giving 2.5 mg (72%) after lyophilisation. Analysis by MS direct injection (solvents: A=water/0.1% TFA and B=acetonitrile/0.1% TFA; 50% B over 2 min; flow 0.3 ml/min, ESI-MS) gave m/z at 1158.5 (MH$^+$) in accordance with the structure.

Example 8

Losartan Derivatised with PEG-Glutaric Acid-cPn216 for Tc-Labelling

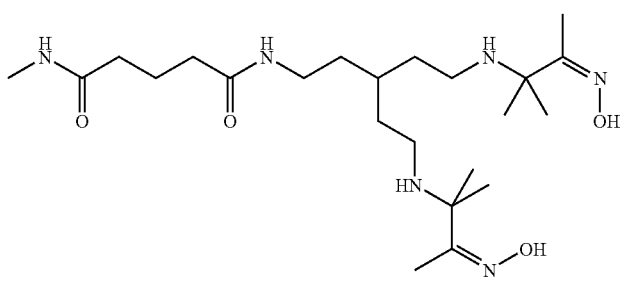

DIEA (2M in NMP, 8 μl, 16 μmol) and a solution of cPn216-succinic acid tetrafluorothiophenyl ester from Example 3b) (5 mg, 8 μmol) in DMF (0.5 ml) were added to a solution of compound from Example 6b) (4 μmol) in DMF (1.5 ml). After stirring overnight the reaction mixture was diluted with water (3 ml) and pH was adjusted to 2 by addition of TFA. The product was purified by preparative HPLC (column Phenomenex Luna C18(2) 5 μm 21.2×250 mm, solvents: A=water/0.1% TFA and B=acetonitrile/0.1% TFA; gradient 20-60% B over 60 min; flow 10.0 ml/min, UV detection at 214 nm) giving 2.0 mg (40%) after lyophilisation. Analysis by MS direct injection (solvents: A=water/0.1% TFA and B=acetonitrile/0.1% TFA; 50% B over 2 min; flow 0.3 m/min, ESI-MS) gave m/z at 1239.8 (MH+) corresponding to the structure.

Compound from Example 6b) (5.0 μmol) was dissolved in methanol (2.5 ml) and pH was adjusted to 9 by addition of DIEA. To the solution was added digclycolic anhydride (Acros, 1.2 mg, 10 μmol). After 50 minutes the reaction mixture was concentrated and the residue was purified by preparative HPLC (column Phenomenex Luna C18(2) 5 μm 21.2×250 mm, solvents: A=water/0.1% TFA and B=acetonitrile/0.1% TFA; gradient 20-60% B over 60 min; flow 10.0 ml/min, UV detection at 214 nm) giving 4.5 mg (98%) of the product. Analysis by MS direct injection (solvents: A=water/0.1% TFA and B=acetonitrile/0.1% TFA; 50% B over 2 min; flow 0.3 ml/min, ESI-MS; m/z 916.9 (MH+)) was in accordance with the structure.

b) Conjugation of cPn216

Compound a) (5 μmol) was dissolved in DMF (2 ml) and activated with HATU (2 mg, 5 μmol) and DIEA (2M in NMP, 5 μl, 10 μmol) for 5 minutes. cPn216 (3.4 mg, 10 μmol) was added (column Phenomenex Luna C18(2) 5 μm 21.2×250 mm, solvents: A=water/0.1% TFA and B=acetonitrile/0.1% TFA; gradient 20-60% B over 60 min; flow 10.0 ml/min, UV

Example 9

Losartan Derivatised with PEG-Diglycolic Acid-cPn216 for Tc-Labelling

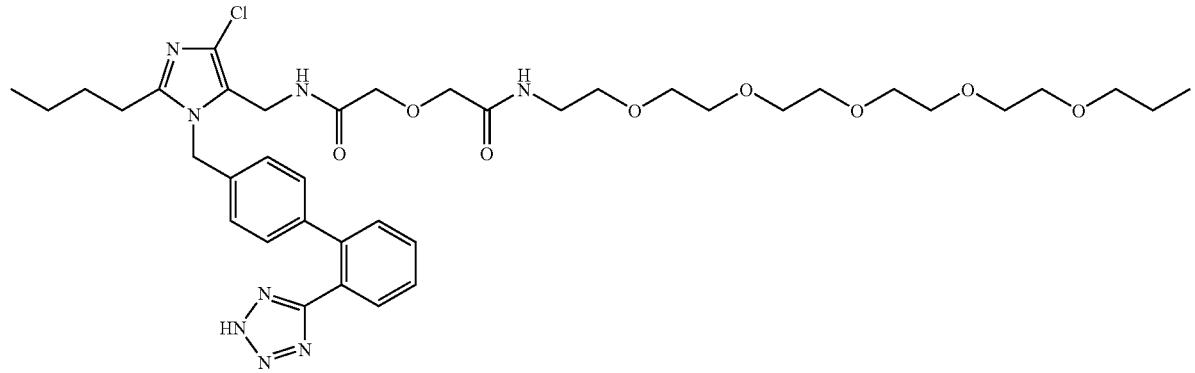

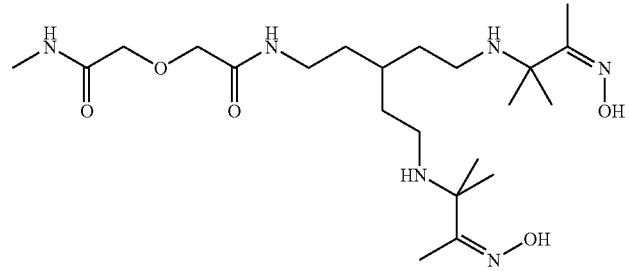

a) Acylation with Diglycolic an Hydride

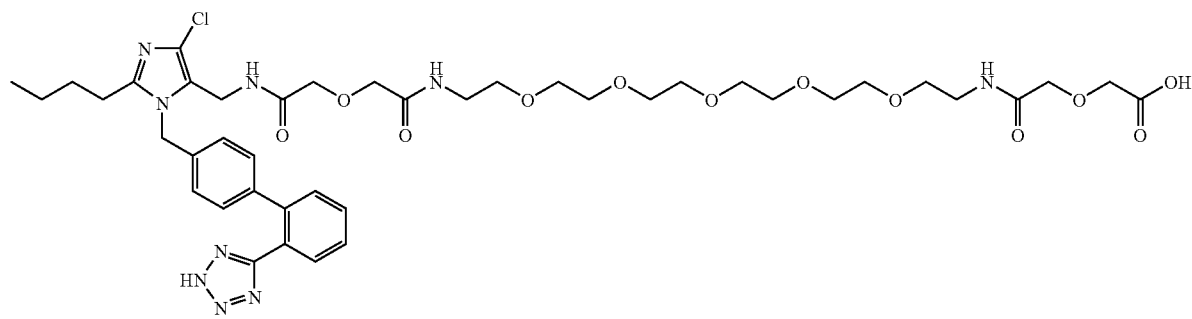

detection at 214 nm) giving 3.7 (57%) mg after lyophilisation. LC-MS analysis (column Phenomenex Luna C18(2) 3 μm 2.0×50 mm, solvents: A=water/0.1% formic acid and B=acetonitrile/0.1% formic acid; gradient 10-40% B over 10 min; flow 1 ml/min, UV detection at 214 nm, ESI-MS) gave a peak at 6.8 minutes with m/z 1241.2 (MH$^+$) corresponding to the structure.

Example 10

Solid Phase Synthesis of Losartan Modified with cPn216 Via a PEG-Glutaric

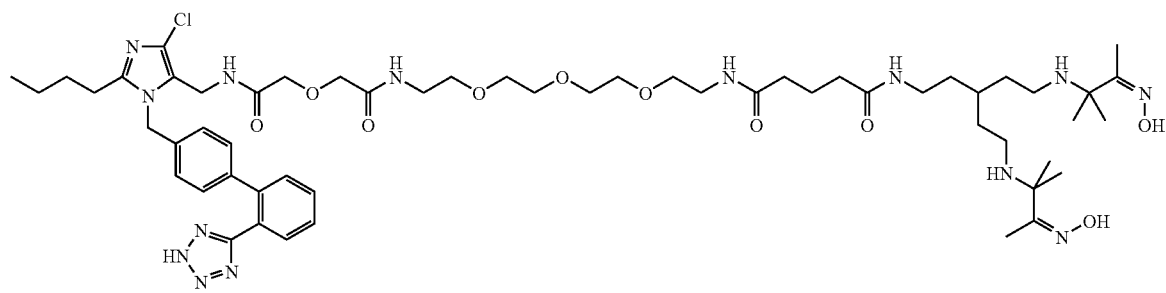

a) Attachment of Losartan to Methoxytrityl Resin b) Azide Formation

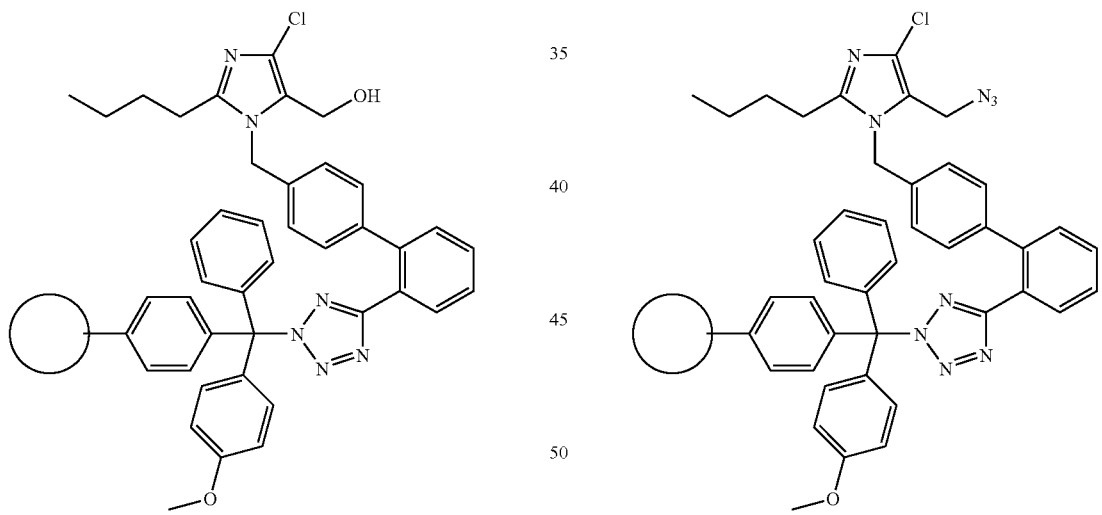

To a suspension of 4-methoxytrityl chloride resin from Novabiochem (53 mg, corresponding to 0.050 mmol) in dichloromethane (1 ml) was added a solution of Losartan (MSD, 42 mg, 0.10 mmol) in DMF (0.5 ml) and DIEA (2 M solution in NMP, 0.10 ml, 0.20 mmol). The mixture was kept at a roller table for 4 days. The resin was drained and washed with DMF and dichloromethane several times. An aliquot of the resin was cleaved (5% TFA and 5% TIS in dichloromethane, 15 min) and analysed by HPLC (column Phenomenex Luna C18(2) 3 μm 4.6×50 mm, solvents: A=water/0.1% TFA and B=acetonitrile/0.1% TFA; gradient 10-80% B over 10 min; flow 2.0 ml/min, UV detection at 214 and 254 nm), giving a peak coeluting with Losartan.

The reaction was carried out in a manual nitrogen bubbler apparatus. To a suspension of the resin from a) above in THF (ca 1 ml) was added DBU (16 μl, 0.11 mmol) and diphenylphosphoryl azide (Aldrich, 13 μl, 0.060 mmol). After ca 30 min fresh aliquots of diphenylphosphoryl azide (7 μl) and DBU (8 μl) were added. After 45 min an aliquot of the resin was cleaved (CH$_2$Cl$_2$/TFA/TIS, 97.5:5:2.5) and analysed by LC-MS (column Phenomenex Luna C18(2) 3 μm 2.0×50 mm, solvents: A=water/0.1% HCOOH and B=acetonitrile/0.1% HCOOH; gradient 10-80% B over 10 min; flow 0.3 ml/min, UV detection at 214 and 254 nm, ESI-MS) giving a peak at 8.8 min with m/z at 447.9 (MH$^+$) corresponding to the azide. No trace of starting material could be observed.

c) Reduction of the Azide to Corresponding Amine

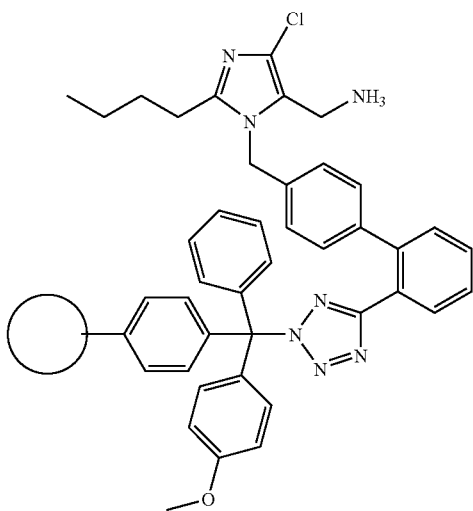

The reaction was run in a manual nitrogen bubbler apparatus. To a solution of tin(II)chloride dihydrate (23 mg, 0.10 mmol) in THF (0.5 ml) was added thiophenol (41 µl, 0.40 mmol) and triethylamine (42 µl, 0.30 mmol). More THF was added until the precipitate was almost dissolved. The mixture was transferred to an aliquot of the resin from b) above (formally corresponding to 0.05 mmol azide) covered with THF (0.5 ml). After 1 hr reaction time the reagent solution was drained off and the resin was washed with THF, DMF and methanol.

An aliquot of the resin was cleaved (CH2Cl2/TFA/TIS, 97.5:5:2.5) and analysed by LC-MS (column Phenomenex Luna C18(2) 3 µm 2.0×50 mm, solvents: A=water/0.1% HCOOH and B=acetonitrile/0.1% HCOOH; gradient 10-80% B over 10 min; flow 0.3 m/min, UV detection at 214 and 254 nm, ESI-MS) showing complete conversion of starting material to a more hydrophilic product eluting at 4.6 min with m/z at 421.7 (MH$^+$) corresponding to the amine.

d) Coupling of the PEG-Glutaryl-cPN216 Units

The reaction was run in a manual nitrogen bubbler apparatus. A mixture of Fmoc-amino PEG-diglycolic acid (Polypure AS, 40 mg, 0.075 mmol), TBTU (24 mg, 0.075 mmol), HOBt (12 mg, 0.075 mmol) and 2 M DIEA in DMF (75 µl, 0.15 mmol) in DMF (0.5 ml) was added to the resin. After two hours the resin was drained and washed with DMF. Kaiser test was negative. The Fmoc group was cleaved by standard treatment with 20% piperidine in DMF. To an aliquot of the resin (formally 0.02 mmol) suspended in DMF (2 ml) were added cPn216-glutaric acid tetrafluorothiophenyl ester from Example 3b) (25 mg, 0.040 mmol), HOBt (6 mg, 0.04 mmol) and 2 M DIEA (30 µl, 0.060 mmol). After two hours reaction time the product was cleaved off the resin (CH$_2$Cl$_2$/TFA/TIS, 97.5:5:2.5). The cleavage solution was concentrated and the residue was purified by preparative HPLC (column Phenomenex Luna C18(2) 5 µm 21.2×250 mm, solvents: A=water/0.1% TFA and B=acetonitrile/0.1% TFA; gradient 20-30% B over 60 min; flow 10.0 ml/min, UV detection at 214 nm) to give 0.1 mg of product after lyophilisation. Analysis by LC-MS (column Phenomenex Luna C18(2) 3 µm 2.0×50 mm, solvents: A=water/0.1% HCOOH and B=acetonitrile/0.1% HCOOH; gradient 10-80% B over 10 min; flow 0.3 ml/min, UV detection at 214 and 254 nm, ESI-MS) gave a peak at 4.3 min with m/z at 1151.4 corresponding to MH$^+$ of the correct structure.

Example 11

Solid Phase Synthesis of Losartan Modified with cPn216 Via a Peg-Glutaric Acid Linker

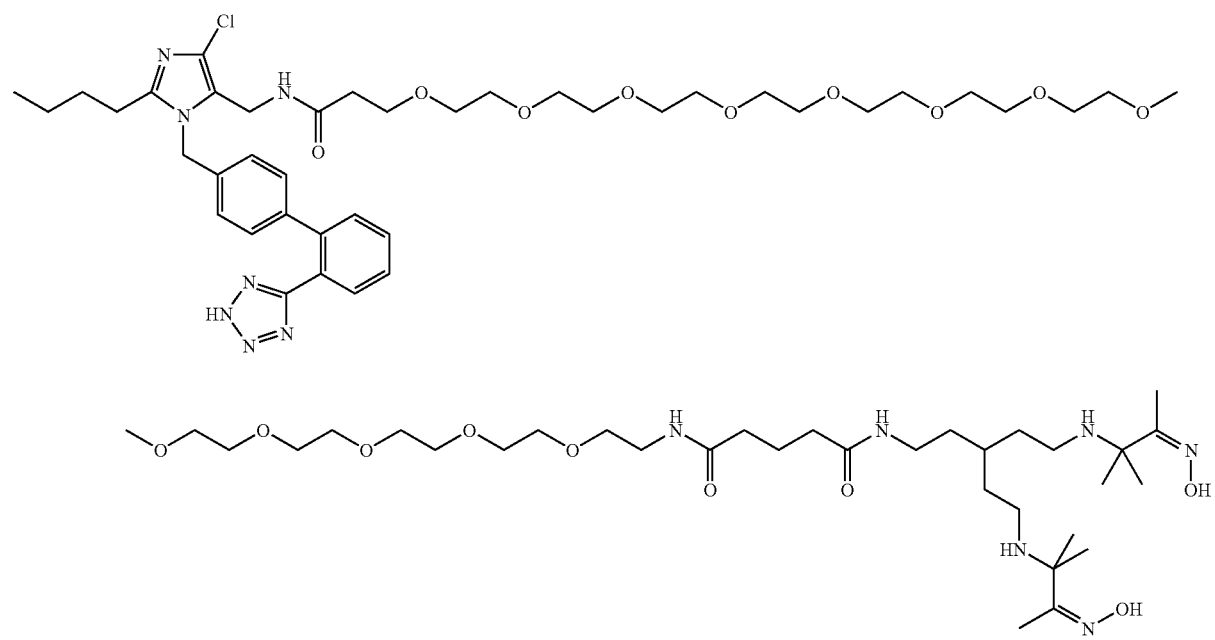

a) Attachment of Losartan to Trityl Derivatised Solid Support

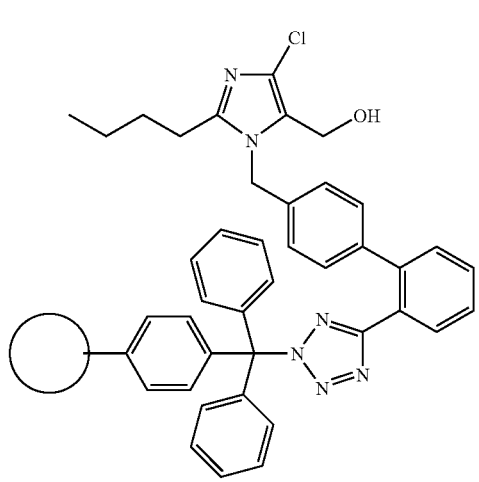

Losartan (MSD, 0.236 g, 0.558 mmol) and triethylamine (Fluka, 0.233 ml, 1.67 mmol) were added to a suspension of trityl chloride resin (Novabiochem, susbstitution 1.24 mmol/g, 0.300 g) in DMF (5 ml). After 4 days the resin was drained and washed. An aliquot of the resin was cleaved (dichloromethane/TFA/triisopropylsilane, 92.5:5.0:2.5, 15 min). HPLC analysis (column Phenomenex Luna C18(2) 3 μm 4.6×50 mm, solvents: A=water/0.1% TFA and B=acetonitrile/0.1% TFA; gradient 10-40% B over 10 min; flow 2.0 ml/min, UV detection at 214 and 254 nm) gave a peak with $t_R$ 6.7 minutes corresponding to Losartan. The resin was treated with dichloromethane/methanol/diisopropylethylamine solution (17:2:1, 20 ml, 1 h), washed with dichloromethane and dried.

b) Replacement of the Hydroxyl Group by Azide

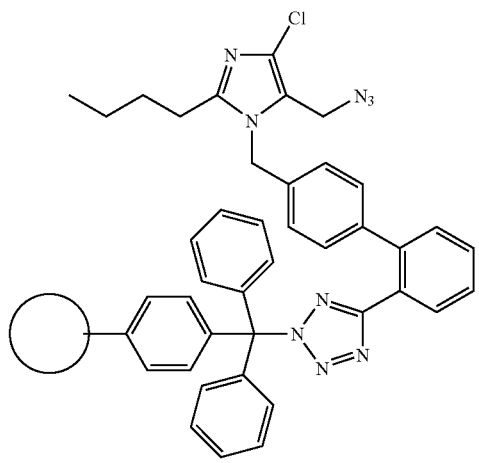

Diphenylphosphoryl azide (Aldrich, 0.481 ml, 2.23 mmol) and DBU (0.611 ml, 4.09 mmol) were added to a suspension of resin bound Losartan from a) (0.372 mmol) in THF (10 ml). The reaction was left over night. An aliquot of the resin was cleaved as described under a). Analysis by LC-MS (column Phenomenex Luna C18(2) 3 μm 50×4.60 mm, solvents: A=water/0.1% TFA and B=acetonitrile/0.1% TFA; gradient 20-80% B over 10 min; flow 1 ml/min, UV detection at 214 nm, ESI-MS) gave a peak, $t_R$ 7.3 minutes, with m/z 448.1 (MH$^+$) corresponding to the structure.

c) Reduction of the Azide Group to Amine

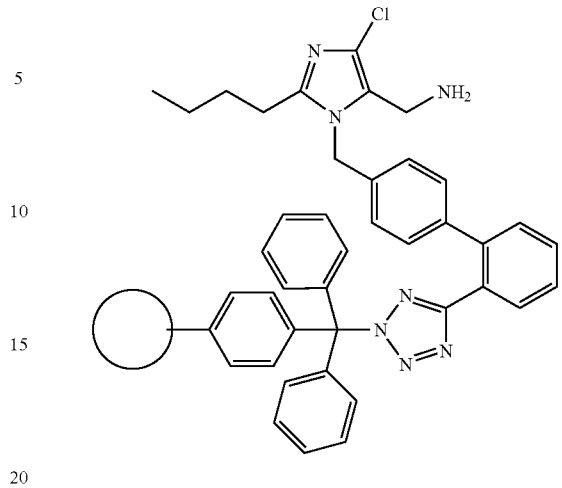

To a suspension of the resin from b) in THF (4 ml) was added addition of tin(II)chloride (Acros, 0.141 g, 0.744 mmol), thiophenol (Fluka, 0.304 ml, 2.976 mmol) and triethylamine (Fluka, 0.311 ml, 2.23 mmol). After 1.5 hour an aliquot of the resin was cleaved as described under a). LC-MS analysis (column Phenomenex Luna C18(2) 3 μm 50×4.60 mm, solvents: A=water/0.1% TFA and B=acetonitrile/0.1% TFA; gradient 20-80% B over 10 min; flow 1 ml/min, UV detection at 214 nm, ESI-MS) gave a peak at 1.9 minutes with m/z 422.2 (MH$^+$) as expected for amine.

d) Conjugation of the PEG-Glutaryl-cPN216 Units

The reaction was run in a manual nitrogen bubbler apparatus. A mixture of Fmoc-PEG propionic acid (Polypure AS, 72 mg, 0.086 mmol), HATU (Applied Biosystems, 33 mg, 0.086 mmol) and DIEA (Fluka, 29 μl, 0.172 mmol) in DMF (2 ml) was added to the resin from c) (0.043 mmol). After 2.5 hours the resin was drained and washed with DMF. Kaiser test was negative. The Fmoc group was cleaved by standard treatment with 20% piperidine in DMF. To the resin in DMF (1.5 ml) were added cPn216-glutaric acid tetrafluorothiophenyl ester from Example 3b) (53 mg, 0.086 mmol) and DIEA (15 μl, 0.086 mmol). The reaction was left over night, Kaiser test was negative. The product was cleaved off the resin (CH2Cl2/TFA/TIS, 97.5:5:2.5). The cleavage solution was concentrated and the product was purified by preparative HPLC (column Phenomenex Luna C18(2) 5 μm 21.2×250 mm, solvents: A=water/0.1% TFA and B=acetonitrile/0.1% TFA; gradient 10-40% B over 60 min; flow 10.0 ml/min, UV detection at 214 nm) giving 3.8 mg after lyophilisation. Analysis by LC-MS (column Phenomenex Luna C18(2) 3 μm 2.0×50 mm, solvents: A=water/0.1% HCOOH and B=acetonitrile/0.1% HCOOH; gradient 10-40% B over 10 min; flow 0.3 ml/min, UV detection at 214 and 254 nm, ESI-MS) gave a peak at 7.2 min with m/z at 1460.6 corresponding to MH$^+$ of the correct structure. Further characterisation was carried out by NMR spectroscopy.

General $^{99m}$Tc-Labelling Protocol

A preparation is made by dissolving 0.1 mg freeze-dried cPn216 derived compound in 0.2 ml (distilled and oxygen-free) water. This solution is transferred into a 10 ml nitrogen filled vial. 0.5 ml carbonate buffer, 0.5 ml Na$^{99m}$TcO$_4$ soluton and 0.1 ml Sn-MDP s The preparation is left at room temperature for 20 minutes.

Carbonate buffer: The carbonate buffer has a pH of 9.2 and contains 8.4 10.6 mg Na$_2$CO$_3$ per ml water. It is purged with nitrogen gas for at least 1 use.

Na$^{99m}$TcO$_4$ solution: Technetium generator (e.g. Ifetec generator) eluate, radioactive concentration of 2 GBq/ml, oxygen free.

Sn-MDP solution: This solution contains 0.131 mg SnCl$_2$*2H$_2$O and 0.925 mg MDP (methylene diphosphonate) per ml water. The solution is made freshly before use under continuous nitrogen gas purging.

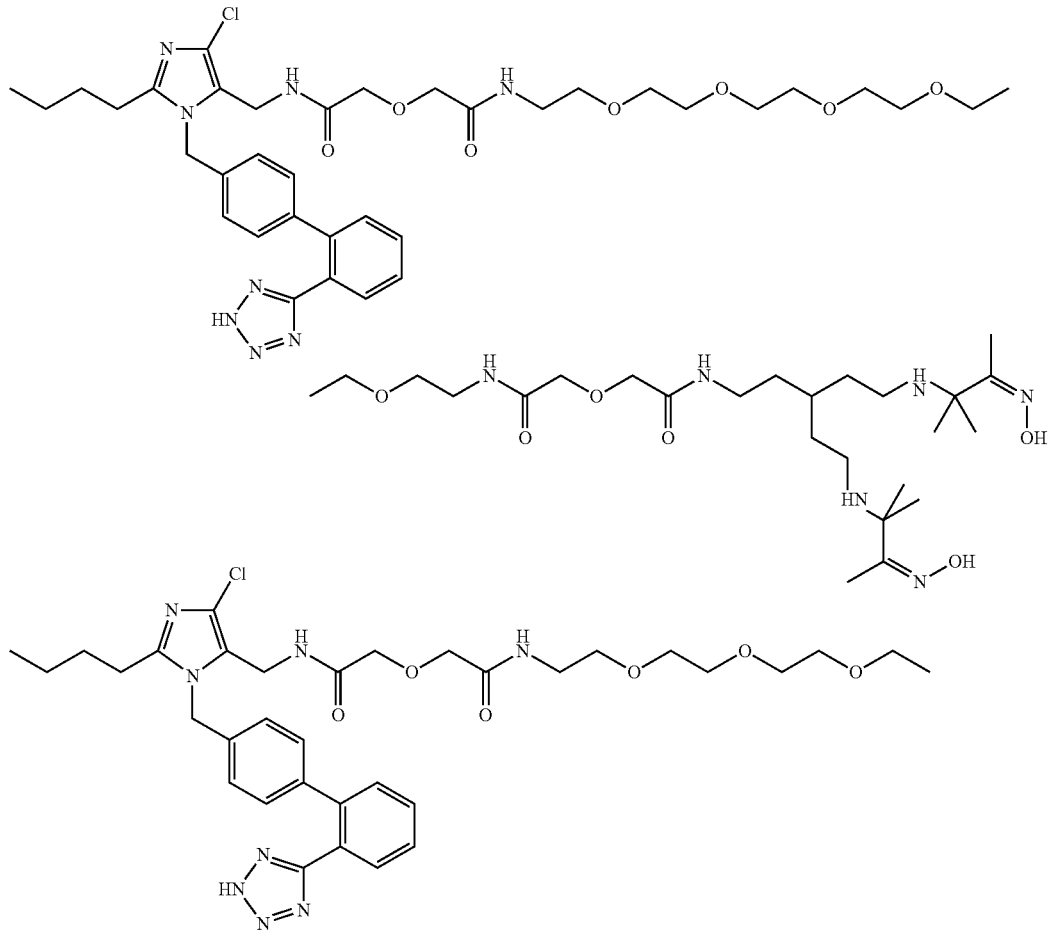

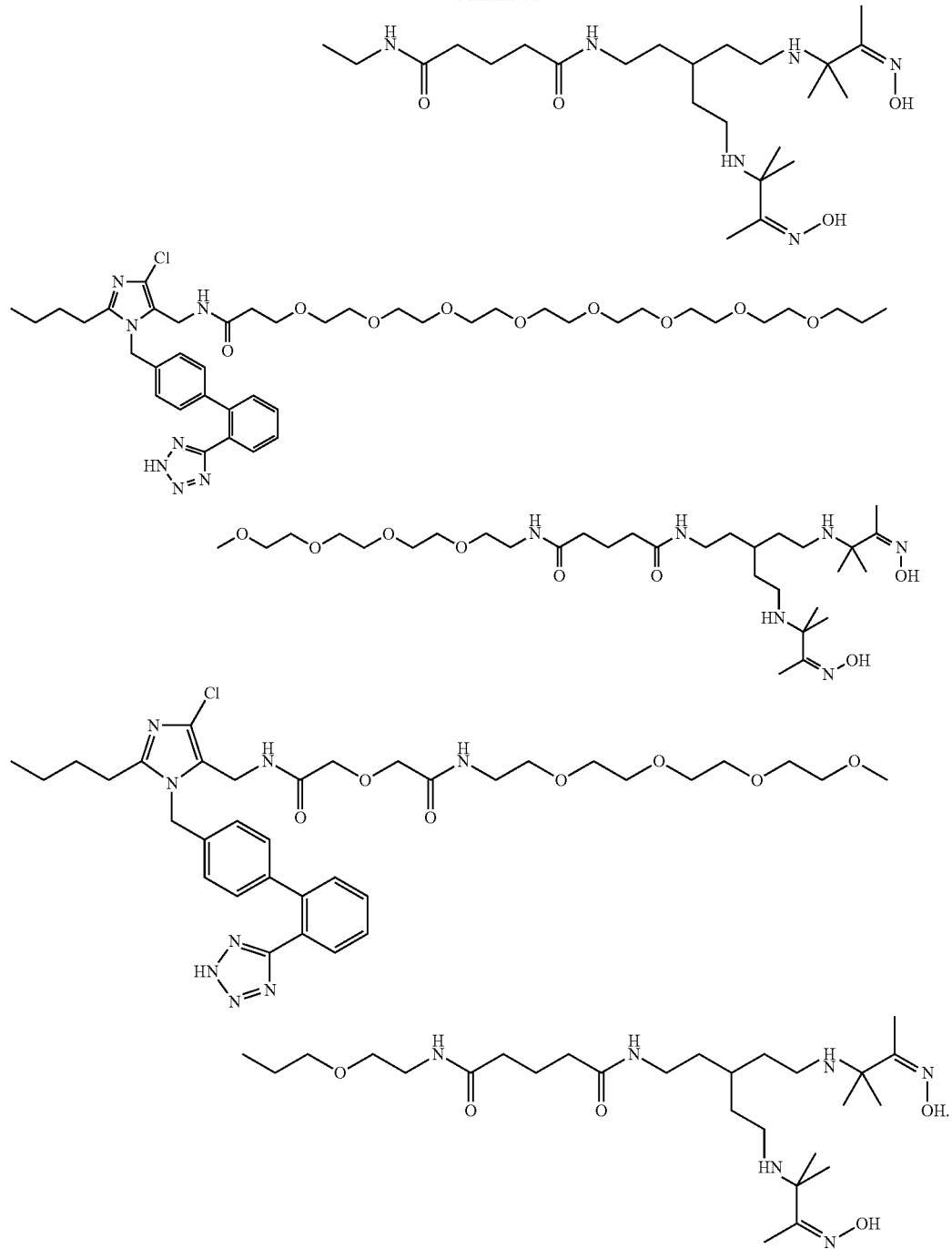

The invention claimed is:

1. A compound of the general formula I:

V-L-Z  Formula I or pharmaceutically acceptable salt thereof, wherein V is a non-peptidic vector having affinity for the Angiotensin II receptor and is selected from Losartan, Valsartan, Candesartan and Eprosartan, L is a bond, a spacer or a linker moiety, and Z represents a chelating agent of Formula e carrying an imageable moiety of a metallic radionuclide M

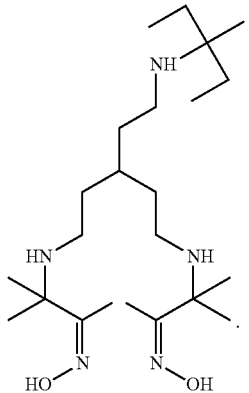

e

2. A pharmaceutical composition comprising an effective amount of a compound of claim 1 or a salt thereof, together with one or more pharmaceutically acceptable adjuvants, excipients or diluents for use in enhancing image contrast in in vivo imaging.

3. A method of generating images of a human or animal body involving administering a contrast agent to said body, and generating an image of at least a part of said body to which said contrast agent has distributed, characterised in that said contrast agent comprises a compound as claimed in claim 1.

4. A method of generating enhanced images of a human or animal body previously administered with a contrast agent composition comprising a compound as claimed in claim 1, which method comprises generating an image of at least part of said body.

5. A compound as claimed in claim 1, wherein M is selected from the group consisting of $^{67}$Ga, $^{111}$In, $^{81m}$Kr, $^{99}$Mo, $^{99m}$Tc and $^{201}$Tl.

6. Compounds as claimed in claim 1 being Tc chelates of compounds of the formulas